US009289613B2

(12) United States Patent
Burnes et al.

(10) Patent No.: US 9,289,613 B2
(45) Date of Patent: Mar. 22, 2016

(54) INTERDEVICE IMPEDANCE

(75) Inventors: John E. Burnes, Coon Rapids, MN (US); Paul G. Krause, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1769 days.

(21) Appl. No.: 12/362,895

(22) Filed: Jan. 30, 2009

(65) Prior Publication Data

US 2010/0114204 A1 May 6, 2010

Related U.S. Application Data

(60) Provisional application No. 61/110,117, filed on Oct. 31, 2008.

(51) Int. Cl.
| A61N 1/36 | (2006.01) |
| A61N 1/37 | (2006.01) |
| A61N 1/365 | (2006.01) |
| A61N 1/08 | (2006.01) |
| A61N 1/372 | (2006.01) |

(52) U.S. Cl.
CPC .............. *A61N 1/37* (2013.01); *A61N 1/36146* (2013.01); *A61N 1/36114* (2013.01); *A61N 1/36521* (2013.01); *A61N 1/37288* (2013.01); *A61N 2001/083* (2013.01)

(58) Field of Classification Search
USPC ............................. 607/2–6, 8–9, 115–117, 28
See application file for complete search history.

(56) References Cited

U.S. PATENT DOCUMENTS

| 4,374,382 A | 2/1983 | Markowitz |
| 4,886,064 A | 12/1989 | Strandberg |
| 4,987,897 A | 1/1991 | Funke |
| 5,113,859 A | 5/1992 | Funke |
| 5,117,824 A | 6/1992 | Keimel et al. |
| 5,261,400 A | 11/1993 | Bardy |
| 5,292,338 A | 3/1994 | Bardy |
| 5,385,576 A * | 1/1995 | Noren et al. ...................... 607/6 |

(Continued)

FOREIGN PATENT DOCUMENTS

| WO | 2006135751 A2 | 12/2006 |
| WO | 2006135791 A2 | 12/2006 |

OTHER PUBLICATIONS

International Search Report and Written Opinion from corresponding PCT Application Serial No. PCT/US2009/062630 mailed Jan. 19, 2010 (13 pages).

(Continued)

*Primary Examiner* — Paula J Stice
(74) *Attorney, Agent, or Firm* — Carol F. Barry

(57) ABSTRACT

An electrical parameter value indicative of an impedance of an electrical path between a first medical device implanted within a patient and a second medical device implanted within the patient may be determined by generating and delivering an electrical signal between electrodes connected to the first medical device and sensing the electrical signal with two or more sense electrodes connected to the second medical device. In some examples, the electrical parameter value indicative of the impedance may be used to detect a system integrity issue, such as relative movement between the first and second medical devices, such as between leads connected to the medical devices, or a lead-related condition. In other examples, the determined impedance may indicate a transthoracic impedance of the patient.

46 Claims, 13 Drawing Sheets

(56) References Cited

U.S. PATENT DOCUMENTS

| | | | |
|---|---|---|---|
| 5,545,186 A | 8/1996 | Olson et al. | |
| 5,755,736 A | 5/1998 | Gillberg et al. | |
| 5,772,605 A * | 6/1998 | Weijand | 600/547 |
| 6,134,470 A | 10/2000 | Hartlaub | |
| 6,415,183 B1 | 7/2002 | Scheiner et al. | |
| 7,305,266 B1 * | 12/2007 | Kroll | 607/28 |
| 7,357,775 B1 | 4/2008 | Koh | |
| 7,387,610 B2 | 6/2008 | Stahmann et al. | |
| 2001/0001126 A1 | 5/2001 | Cammilli et al. | |
| 2002/0120307 A1 * | 8/2002 | Jorgenson et al. | 607/27 |
| 2002/0123674 A1 | 9/2002 | Plicchi et al. | |
| 2003/0004552 A1 * | 1/2003 | Plombon et al. | 607/27 |
| 2004/0220628 A1 | 11/2004 | Wagner | |
| 2005/0080460 A1 | 4/2005 | Wang et al. | |
| 2005/0149133 A1 | 7/2005 | Libbus et al. | |
| 2005/0197680 A1 | 9/2005 | DelMain et al. | |
| 2006/0031378 A1 | 2/2006 | Vallapureddy et al. | |
| 2006/0095080 A1 | 5/2006 | Libbus et al. | |
| 2006/0224187 A1 * | 10/2006 | Bradley et al. | 607/2 |
| 2006/0241699 A1 | 10/2006 | Libbus et al. | |
| 2007/0150011 A1 | 6/2007 | Meyer et al. | |
| 2007/0239215 A1 | 10/2007 | Bhunia et al. | |
| 2007/0239229 A1 | 10/2007 | Masoud et al. | |
| 2007/0260283 A1 | 11/2007 | Li | |
| 2008/0015659 A1 | 1/2008 | Zhang et al. | |
| 2008/0021507 A1 | 1/2008 | Libbus et al. | |
| 2008/0091114 A1 * | 4/2008 | Min et al. | 600/508 |
| 2008/0125826 A1 | 5/2008 | Belalcazar et al. | |
| 2008/0147140 A1 | 6/2008 | Ternes et al. | |
| 2008/0167696 A1 | 7/2008 | Cates et al. | |
| 2008/0215118 A1 | 9/2008 | Goetz et al. | |
| 2009/0012416 A1 | 1/2009 | Belalcazar et al. | |
| 2009/0026201 A1 | 1/2009 | Hall et al. | |

OTHER PUBLICATIONS

U.S. Appl. No. 61/110,117, filed Oct. 31, 2008 entitled "Interdevice Impedance", by Burnes et al.

International Preliminary Report on Patentability from international application No. PCT/2009/062630, dated May 12, 2011, 8 pp.

* cited by examiner

INTERDEVICE IMPEDANCE

This application claims the benefit of U.S. Provisional Application No. 61/110,117, entitled, "INTERDEVICE IMPEDANCE," and filed on Oct. 31, 2008, the entire content of which is incorporated herein by reference.

TECHNICAL FIELD

The invention relates to medical devices, and, more particularly, systems including two or more medical devices.

BACKGROUND

A wide variety of implantable medical devices that deliver a therapy or monitor a physiologic condition of a patient have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, at least some of which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead. A proximal portion of the lead may be coupled to an implantable medical device housing, which may contain electronic circuitry such as stimulation generation and/or sensing circuitry. In some cases, electrodes or sensors may be positioned on an IMD housing as an alternative or in addition to electrodes or sensors deployed on one or more leads.

For example, implantable cardiac devices, such as cardiac pacemakers or implantable cardioverter defibrillators, provide therapeutic electrical stimulation to the heart by delivering electrical therapy signals such as pulses or shocks for pacing, cardioversion or defibrillation pulses via electrodes of one or more implantable leads. In some cases, an implantable cardiac device may sense intrinsic depolarizations of the heart, and control the delivery of therapeutic stimulation to the heart based on the sensing. When an abnormal rhythm of the heart is detected, such as bradycardia, tachycardia or fibrillation, an appropriate electrical therapy (e.g., in the form of pulses or shocks) may be delivered to restore the normal rhythm. For example, in some cases, an implantable medical device may deliver pacing, cardioversion or defibrillation therapy to the heart of the patient upon detecting ventricular tachycardia, and deliver cardioversion or defibrillation electrical therapy to a patient's heart upon detecting ventricular fibrillation.

SUMMARY

In general, the disclosure is directed toward therapy systems that deliver electrical stimulation therapy to a tissue site within a patient and cardiac rhythm management therapy to a heart of a patient. The tissue site for the electrical stimulation therapy may be, for example, a nonmyocardial tissue site or nonvascular cardiac tissue site (e.g., a cardiac fat pad). In some examples, the therapy system may include a first implantable medical device (IMD) that delivers electrical stimulation to the tissue site within a patient, such as a tissue site proximate a nerve (e.g., a vagus nerve or a spinal cord) or another tissue site, and a second implantable medical device (IMD) that delivers cardiac rhythm management therapy, such as at least one of pacing, cardioversion or defibrillation therapy to a heart of the patient. The ICD may deliver any combination of pacing, cardioversion, and defibrillation pulses. The first and second implantable medical devices are not physically connected each other. The first IMD may be referred to as an implantable neurostimulator (INS) or an electrical stimulator, and the second IMD may be referred to as an implantable cardiac device (ICD).

In some examples, the ICD may generate and transmit electrical signals between electrodes coupled to the ICD (e.g., via one or more leads or on a housing of the ICD), where the electrical signals may have an intensity that is less than a threshold associated with activation of tissue (e.g., a nerve, muscle, etc.) of a patient in which the ICD and INS are implanted. In some examples, the intensity of the electrical signals may have a threshold that is less than a perception threshold of the patient. The INS may sense the electrical signal generated between electrodes connected to the ICD. The electrical signal sensed by the INS may be useful for various purposes, such as facilitating communication between the ICD and INS or determining an electrical parameter value indicative of an impedance of an electrical path between the ICD and INS.

The electrical parameter value indicative of the interdevice impedance may be indicative of intrathoracic impedance (also referred to as "transthoracic impedance") of the patient or a system integrity (e.g., lead integrity) issue. The electrical path may include a path between the ICD and INS, between electrodes electrically connected to the ICD or INS and the housings of the INS or ICD, respectively, or between electrodes electrically connected to the ICD and electrodes electrically connected to the INS. A value indicative of the impedance of the electrical path may indicate a relative position between electrodes coupled to the ICD and INS.

In other examples, the INS may generate and transmit electrical signals between electrodes connected to the INS, where the electrical signals have an intensity that is less than an activation threshold of the proximate nerve and/or a perception threshold of the patient. The ICD may sense the electrical signal generated between the electrodes connected to the INS and demodulate the electrical signals to extract information from the signals or determine an electrical parameter value indicative of an impedance of an electrical path between the ICD and INS based on the sensed electrical signals.

In one aspect, the disclosure is directed toward a method comprising delivering an electrical signal between a first electrode and a second electrode of a first implantable medical device, sensing the electrical signal with a second implantable medical device, and determining an electrical parameter value indicative of an impedance of a path between the first and second implantable medical devices based on the sensed electrical signal.

In another aspect, the disclosure is directed toward a system comprising a first implantable medical device connected to a first electrode and a second electrode, wherein the first implantable medical device generates an electrical signal between the first and second electrodes, a second implantable medical device that senses the electrical signal, and a processor that determines an electrical parameter value indicative of an impedance of a path between the first and second implantable medical devices based on the sensed electrical signal.

In another aspect, the disclosure is directed toward a system comprising means for delivering an electrical signal between a first electrode and a second electrode of a first implantable medical device, means for sensing the electrical signal at a second implantable medical device, and means for determining an electrical parameter value indicative of an impedance of a path between the first and second implantable medical devices based on the sensed electrical signal.

In another aspect, the disclosure is directed toward a method comprising sensing an electrical signal with an electrode connected to a first implantable medical device, where the electrical signal is generated by a second implantable medical device that is different than the first implantable medical device and determining an electrical parameter value indicative of an impedance of a path between the first and second implantable medical devices based on the sensed electrical signal.

In another aspect, the disclosure is directed toward a computer-readable medium comprising instructions. The instructions cause a programmable processor to perform any part of one or more of the techniques described herein.

The details of one or more examples are set forth in the accompanying drawings and the description below. Other features, objects, and advantages of the disclosure will be apparent from the description and drawings, and from the claims.

DETAILED DESCRIPTION

Some medical device systems may include a neurostimulator or another electrical stimulator in addition to an implantable cardiac device that delivers cardiac rhythm therapy to a patient. For example, a medical device system may include a spinal cord stimulator and an implantable atrial defibrillator, whereby the spinal cord stimulator may deliver stimulation to reduce pain associated with delivery of defibrillation shocks. As another example, a medical device system may include an electrical stimulator that provides electrical stimulation to modulate an autonomic nervous system of the patient in an attempt to influence cardiac function. In this way, electrical stimulation in addition to cardiac rhythm therapy that is delivered to the heart of the patient may complement anti-tachyarrhythmia treatments, such as antitachycardia pacing, cardioversion or defibrillation.

Figure 1:
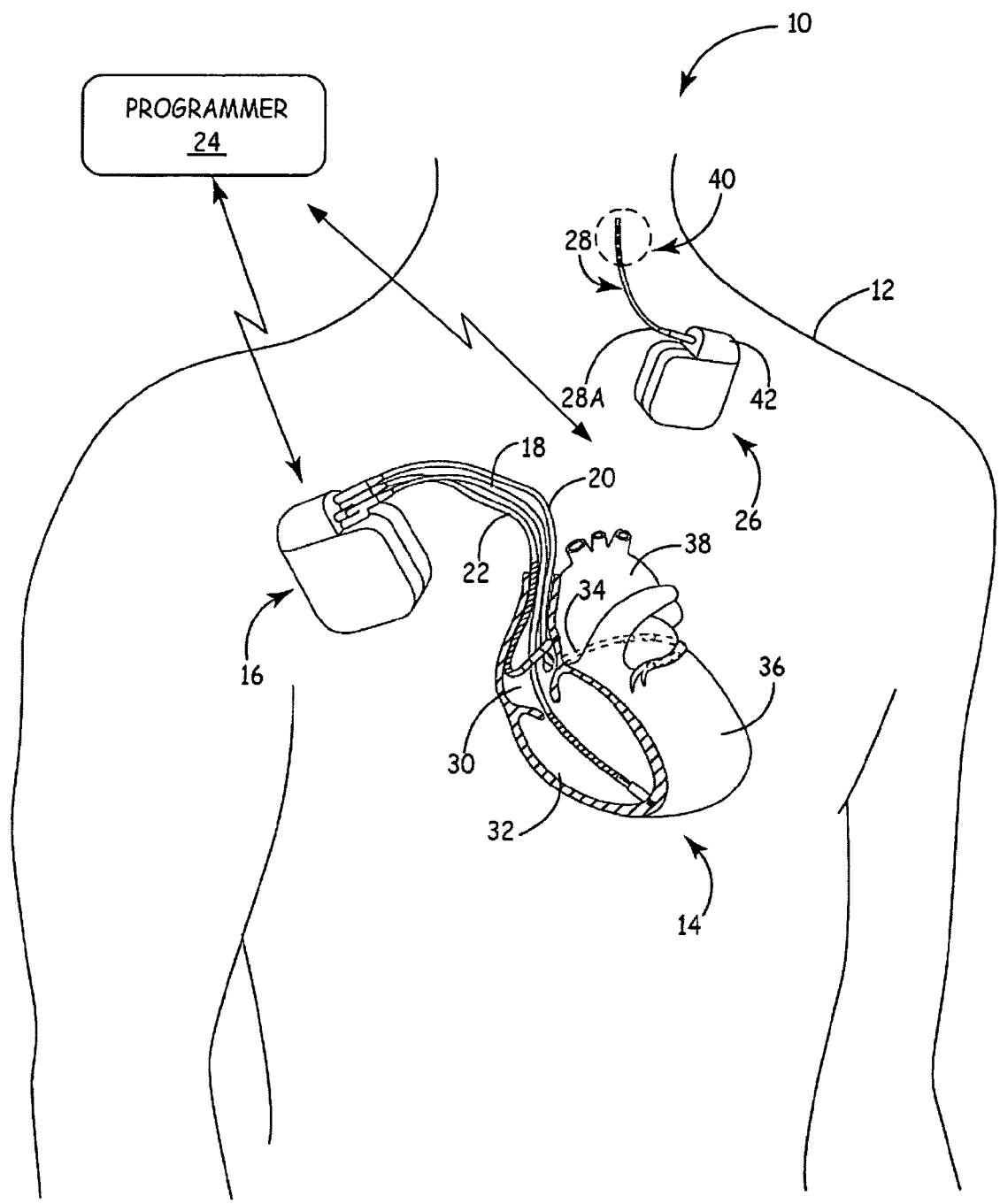
FIG. 1 is a conceptual diagram illustrating an example therapy system that includes an implantable cardiac device (ICD) and an implantable neurostimulator (INS).

FIG. 1 is a conceptual diagram illustrating an example therapy system 10 that may be used to provide therapy to patient 12. Patient 12 ordinarily, but not necessarily, will be a human. Therapy system 10 includes implantable cardiac device (ICD) 16, which is connected (or "coupled") to leads 18, 20, and 22, and programmer 24. ICD 16 may comprise, for example, an implantable pacemaker, cardioverter, and/or defibrillator that generates and delivers electrical signals to heart 14 of patient 12 via electrodes connected to one or more of leads 18, 20, and 22. In some examples, ICD 16 may deliver pacing pulses, but not cardioversion or defibrillation pulses, while in other examples, ICD 16 may deliver cardioversion or defibrillation pulses, but not pacing pulses. In addition, in further examples, ICD 16 may deliver pacing, cardioversion, and defibrillation pulses. In various examples, ICD 16 may deliver pacing that includes one or both of anti-tachycardia pacing (ATP) and cardiac resynchronization therapy (CRT).

Therapy system 10 further comprises implantable electrical stimulator 26, which is coupled to lead 28. Electrical stimulator 26 may also be referred to as an implantable neurostimulator (INS) 26, although INS 26 may not deliver electrical stimulation to a target nerve site in all examples. In general, INS 26 may be any suitable implantable medical device (IMD) that includes a signal generator that generates electrical stimulation signals that may be delivered to a nonmyocardial tissue site or a nonvascular cardiac tissue site of patient 12. A nonmyocardial tissue site may include a tissue site that does not include cardiac muscle (e.g., the myocardium). For example, a nonmyocardial tissue site may be proximate a muscle other than cardiac muscle, an organ other than the heart, or neural tissue. Examples of nonmyocardial tissue sites and nonvascular tissue sites include, but are not limited to, tissue proximate a nerve, a spinal cord, a muscle, subcutaneous tissue, or heart 14 of patient 12. The nonmyocardial tissue site may include extravascular tissue sites or intravascular tissue sites. An extravascular tissue site may be outside of heart 14 and outside of arteries, veins, or other vasculature of patient 12, whereas an intravascular tissue site may be within heart 14 or within arteries, veins or other vasculature of patient 12.

A tissue site proximate a nerve may be a neural tissue site to which delivery of electrical stimulation may activate the nerve. In some examples, a tissue site proximate a nerve may be in a range of about zero centimeters to about ten centimeters from the nerve, although other distance ranges are contemplated and may depend upon the nerve. The nonmyocardial tissue site may include extravascular tissue sites or intravascular tissue sites. A nonvascular cardiac tissue site may include, for example, a cardiac fat pad.

In some examples, delivery of electrical stimulation to a nonmyocardial tissue site or a nonvascular cardiac tissue site (e.g., proximate a nerve or not be proximate a nerve) may help modulate an autonomic nervous system of patient 12. In some examples, INS 26 may deliver electrical stimulation therapy to a nerve of patient 12 via a lead implanted within vasculature (e.g., a blood vessel) of patient 12. In some examples, INS 26 may deliver electrical stimulation that is delivered to peripheral nerves that innervate heart 14, or fat pads on heart 14 that may contain nerve bundles. In the example shown in FIG. 1, electrodes of lead 28 are positioned outside the vasculature of patient 12 and positioned to deliver electrical stimulation to a vagus nerve (not shown) of patient 12. Stimulation may be delivered to extravascular tissue sites, for example, when lead 28 is not implanted within vasculature, such as within a vein, artery or heart 14. In other examples, stimulation may be delivered to a tissue site via electrodes of an intravascular lead that is implanted within vasculature.

Although INS 26 is referred to throughout the remainder of the disclosure as a "neurostimulator" and as delivering neurostimulation pulses, in other examples, INS 26 may deliver electrical stimulation to any suitable nonmyocardial or nonvascular cardiac tissue site within patient 12, which may or may not be proximate a nerve.

Figure 6:
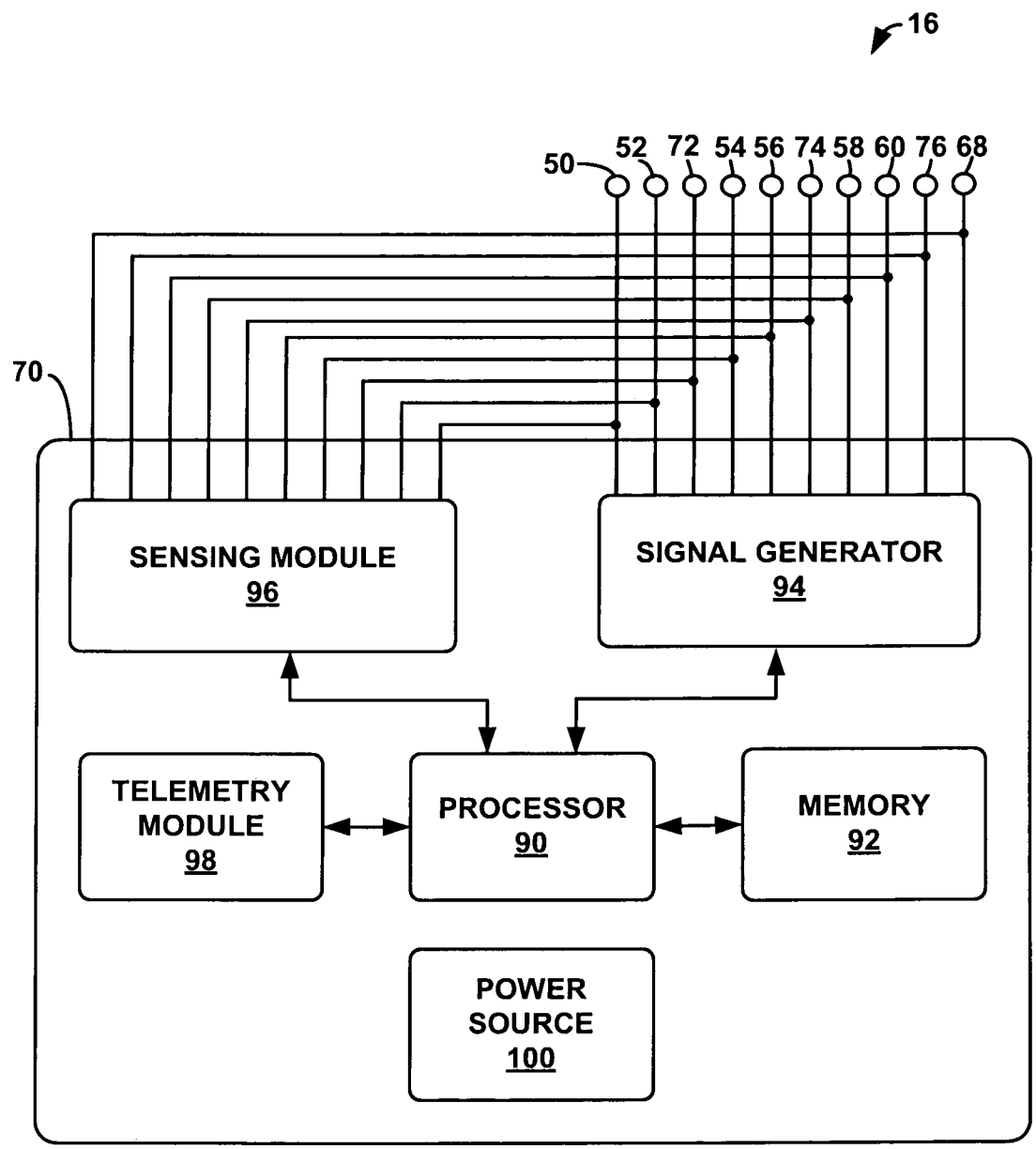
FIG. 6 is a functional block diagram of an example ICD that generates and delivers electrical stimulation to a heart of a patient.
Figure 7:
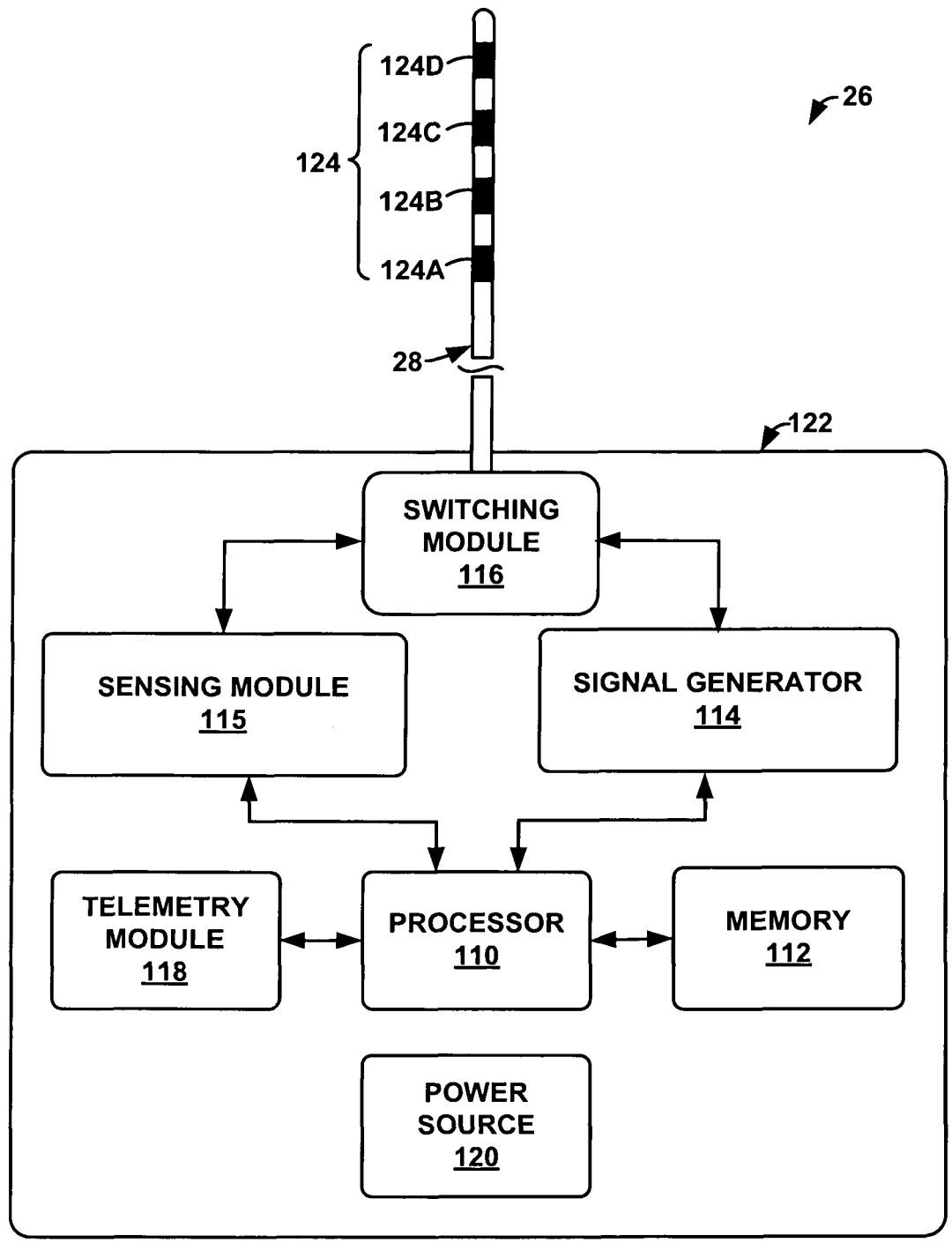
FIG. 7 is a functional block diagram of an example INS that generates and delivers electrical stimulation signals to a target tissue site other than cardiac tissue of a patient.

ICD 16 and INS 26 are not physically connected to each other and each includes respective housings that substantially enclose components, such as a processor, memory, signal generator, etc., which are described with respect to FIGS. 6 and 7. Moreover, in the example shown in FIG. 1, the ICD 16 is not mechanically connected to the electrodes of lead 28 and INS 26 is not mechanically connected to the electrodes of leads 18, 20, 22.

Leads 18, 20, 22 that are coupled to ICD 16 extend into the heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. As described in further detail with reference to FIG. 5, in other examples, ICD 16 may deliver stimulation therapy to heart 14 by delivering stimulation to an extravascular tissue site in addition to or instead of delivering stimulation via electrodes of intravascular leads 18, 20, 22.

ICD 16 may sense electrical signals attendant to the depolarization and repolarization of heart 14 via electrodes (not shown in FIG. 1) coupled to at least one of the leads 18, 20, 22. In some examples, ICD 16 provides pacing pulses to heart 14 based on the electrical signals sensed within heart 14. These electrical signals sensed within heart 14 may also be referred to as cardiac signals or electrical cardiac signals. The configurations of electrodes used by ICD 16 for sensing and pacing may be unipolar or bipolar. ICD 16 may also provide defibrillation therapy and/or cardioversion therapy via electrodes located on at least one of the leads 18, 20, 22. ICD 16 may detect arrhythmia of heart 14, such as fibrillation of ventricles 32 and 36, and deliver defibrillation therapy to heart 14 in the form of electrical pulses. In some examples, ICD 16 may be programmed to deliver a progression of therapies, e.g., pulses with increasing energy levels, until a fibrillation of heart 14 is stopped. ICD 16 may detect fibrillation employing one or more fibrillation detection techniques known in the art.

In the example of FIG. 1, INS 26 has been implanted in patient 12 proximate to a target stimulation site 40, such as a tissue site proximate a vagus nerve (not shown). For example, INS 26 may be subcutaneously or submuscularly implanted in the body of a patient 12 (e.g., in a chest cavity, lower back, lower abdomen, or buttocks of patient 12). INS 26 provides a programmable stimulation signal (e.g., in the form of electrical pulses or a continuous signal) that is delivered to target stimulation site 40 by implantable medical lead 28, and more particularly, via one or more stimulation electrodes carried by lead 28. INS 26 may also be referred to as a signal generator, stimulation generator or an electrical stimulator. Proximal end 28A of lead 28 may be both electrically and mechanically coupled to connector 42 of INS 26 either directly or indirectly (e.g., via a lead extension). In particular, conductors disposed in the lead body may electrically connect stimulation electrodes (and sense electrodes, if present) of lead 28 to INS 26. In some examples, lead 28 may also carry one or more sense electrodes to permit INS 26 to sense electrical signals from target stimulation site 40. Furthermore, in some embodiments, INS 26 may be coupled to two or more leads, e.g., for bilateral or multi-lateral stimulation.

Delivery of electrical stimulation by INS 26 to one or more nonmyocardial or nonvascular cardiac tissues sites, e.g., proximate to a nerve, nerve site, cardiac fat pad, or an extravascular target tissue site that is not proximate a nerve, may provide cardioprotective benefits to patient 12. For example, delivery of electrical stimulation to a tissue site proximate a nerve of patient 12 may help treat heart failure (e.g., congestive heart failure or high output cardiac failure). In addition, delivery of electrical stimulation to a tissue site proximate a nerve of patient 12 to modulate an autonomic nervous system of patient 12 may help reduce or eliminate cardiovascular conditions such as bradycardia, tachycardia, unhealthy cardiac contractions, ischemia, inefficient heart pumping, inefficient collateral circulation of heart 14 or cardiac muscle trauma.

Delivery of electrical stimulation by INS 26 may also complement antitachycardia therapy (e.g., antitachycardia pacing, cardioversion or defibrillation) by ICD 16 or provide back-up therapy to the cardiac rhythm therapy provided by ICD 16. For example, if ICD 16 is unavailable to provide therapy to patient 12, e.g., due to a low power level, INS 26 may deliver therapy to patient 12 to help terminate or prevent a cardiac event (e.g., tachycardia).

In some examples, INS 26 may deliver electrical stimulation to peripheral nerves that innervate heart 14, or fat pads on heart 14 that may contain nerve bundles. In the example shown in FIG. 1, INS 26 provides electrical stimulation therapy of a parasympathetic nerve, such as a vagus nerve, of patient 12. Stimulation of a parasympathetic nerve of patient 12 may help control a heart rate of heart 14 (e.g., to increase or decrease the heart rate), which may or otherwise control cardiac function. In this way, stimulation of a parasympathetic nerve may complement antitachyarrhythmia therapy (e.g., antitachycardia pacing, cardioversion or defibrillation) delivered by ICD 16.

In other examples, electrodes of lead 28 may be positioned to deliver electrical stimulation to any other suitable nerve, organ, muscle or muscle group in patient 12, which may be selected based on, for example, a therapy program or regimen selected or prescribed for a particular patient. In some examples, INS 26 may deliver electrical stimulation to other sympathetic or parasympathetic nerves, baroreceptors, or the carotid sinus or a cardiac branch of the vagal trunk of patient 12 in order to complement the delivery of therapy by ICD 16. In addition, in some examples, INS 26 may deliver electrical stimulation to a peripheral nerve field site, whereby electrodes 124 (FIG. 7) of lead 28 are implanted in a region where patient 12 experiences pain. The pain may be related to stimulation delivered by ICD 16 or a patient condition, such as angina or chronic back pain.

Figure 2:
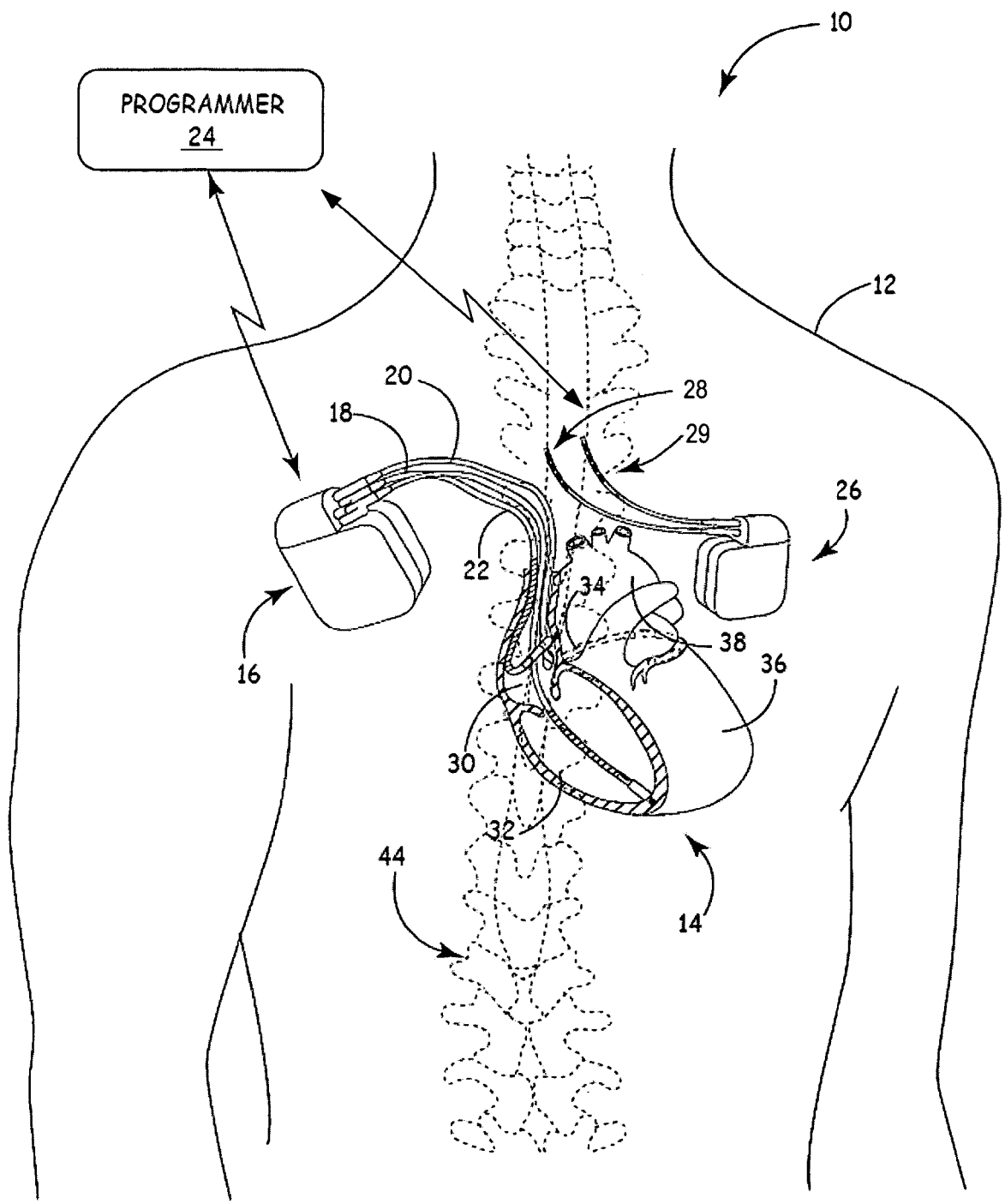
FIG. 2 is a conceptual diagram illustrating another example therapy system that includes an ICD and an INS.

As another example, as shown in FIG. 2, INS 26 may deliver electrical stimulation to spinal cord 44 of patient 12. In the example shown in FIG. 2, INS 26 is coupled to two leads 28, 29, which may facilitate bilateral stimulation spinal cord stimulation of patient 12. In other examples, INS 26 may be coupled to a single lead 28, 29 or more than two leads. Although leads 28, 29 are shown to be introduced into spinal cord 44 via the thoracic column in the example shown in FIG. 2, in other examples, leads 28, 29 may be introduced into spinal cord 44 near the lumbar region. Electrodes of leads 28, 29 may be positioned within an intrathecal space or epidural space of spinal cord 44, or, in some examples, adjacent nerves that branch off of spinal cord 44. In some examples, leads 28, 29 are implanted within patient 12 and positioned such that electrodes of leads 28, 29 deliver electrical stimulation to locations proximate to the T1 to T6 thoracic vertebrae of the patient's vertebral column. For example, electrodes of at least one of the leads 28, 29 may span the T3 to T6 thoracic vertebrae or deliver electrical stimulation to a tissue site proximate at least one of the T3 to T6 thoracic vertebrae. In other examples, leads 28, 29 may be implanted to deliver electrical stimulation to other regions proximate or within spinal cord 44, such as over or near other vertebrae.

Stimulation of spinal cord 44 or nerves branching therefrom by INS 26 may help prevent or mitigate occurrences of tachyarrhythmias and may reduce the level of aggressiveness of the cardiac rhythm therapy, such as pacing, cardioversion or defibrillation, delivered by ICD 16. In this way, ICD 16 and INS 26 may operate in conjunction with each other to help prevent arrhythmias of heart 14 of patient 12, as well as to terminate detected arrhythmias.

In some examples, INS 26 delivers therapy to patient 12 with a voltage amplitude of about 0.2 volts to about 12 volts, a pulse duration of about 40 microseconds (μs) to about 600 μs, such as about 50 μs to about 500 μs), and a pulse rate of 1 to 100 Hertz (Hz) (e.g., 10 Hz to 100 Hz). However, other stimulation parameter values for INS 26 are contemplated. INS 26 may deliver electrical stimulation to patient 12 substantially continuously or periodically. In some examples, INS 26 may deliver electrical stimulation to patient 12 based on the timing of electrical stimulation by ICD 16, such as prior to the delivery of electrical stimulation (e.g., antitachycardia pacing or a defibrillation or cardioversion pulse) by ICD 16, during the delivery of electrical stimulation by ICD 16, subsequent to the delivery of electrical stimulation by ICD 16 or any combination of the aforementioned times. In addition, in some examples, INS 26 may deliver electrical stimulation to patient 12 based on a sensed event or, such as atrial or ventricular depolarization, or based on a sensed physiological condition. The event or physiological condition may be sensed by ICD 16, INS 26 or another sensing device.

ICD 16 and INS 26 may communicate with each other in order for INS 26 to time the delivery of electrical stimulation based on the delivery of stimulation pulses by ICD 16, where the stimulation pulses may be pacing pulses or cardioversion/defibrillation pulses. ICD 16 and INS 26 may communicate directly or indirectly (e.g., via an intermediate device, such as programmer 24) using any suitable communication technique. Examples communication techniques that may be implemented to facilitate communication between ICD 16 and INS 26 may include, for example, radiofrequency (RF) communication techniques, optical communication techniques, ultrasonic communication techniques, and the like. Communication signals may also be transmitted between ICD 16 and INS 26 via electrical signals generated between electrodes. For example, ICD 16 may generate an electrical signal between electrodes of leads 18, 20, and/or 22, and INS 26 may receive the signal by sensing the electrical signal via electrodes of leads 28 and/or 29. Similarly, INS 26 may generate an electrical signal between electrodes of leads 28 and/or 29, and ICD 16 may receive the signal by sensing the electrical signal via electrodes of leads 18, 20, and/or 22. The sensed signal may be demodulated in order to extract information therefrom. Communication between ICD 16 and INS 26 may be periodic, e.g., according to a regular schedule, or on an as-needed basis, e.g., when INS 26 delivers electrical stimulation to patient 12.

In other examples, INS 26 may deliver electrical stimulation to patient 12 independently of the cardiac rhythm therapy delivered by ICD 16. For example, INS 26 may be programmed to deliver electrical stimulation to patient 12 according to a schedule that is determined independently of the actual delivery of stimulation pulses by ICD 16. The schedule may be determined, for example, by a clinician based on a trial stimulation period in which multiple therapy schedules for INS 26 are tested on patient 12. The schedule may dictate when INS 26 actively delivers electrical stimulation to patient 12 and when INS 26 does not actively deliver electrical stimulation to patient 12. For example, the schedule may include a mandatory sleep period for INS 26 during which INS 26 reverts to a relatively low-power sleep mode. During the sleep mode, INS 26 may not deliver therapy to patient 12 or may deliver a relatively minimal amount of electrical stimulation therapy to patient 12. The sleep period may be, for example, when patient 12 is sleeping or otherwise has a relatively low activity level. The sleep period may be useful for conserving the power source of INS 26.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with ICD 16 and/or INS 26. For example, the user may interact with programmer 24 to retrieve physiological or diagnostic information from ICD 16 and/or INS 26. A user may also interact with programmer 24 to program ICD 16 and INS 26, e.g., select values for operational parameters of ICD 16 and INS 26, respectively.

For example, the user may use programmer 24 to retrieve information from ICD 16 regarding the rhythm of heart 14, trends therein over time, or tachyarrhythmia episodes. As another example, the user may use programmer 24 to retrieve information from ICD 16 regarding other sensed physiological parameters of patient 12, such as electrical depolarization/repolarization signals from the heart (referred to as "electrogram" or EGM), intracardiac or intravascular pressure, activity, posture, respiration, or thoracic impedance. As another example, the user may use programmer 24 to retrieve information from ICD 16 regarding the performance or integrity of ICD 16 or other components of system 10, such as leads 18, 20, and 22, or a power source of ICD 16.

The user may use programmer 24 to program a therapy progression, select electrodes used to deliver defibrillation pulses, select waveforms for the defibrillation pulse, or select or configure a fibrillation detection algorithm for ICD 16. The user may also use programmer 24 to program aspects of other therapies provided by ICD 16, such as cardioversion or pacing therapies. For example, with the aid of programmer 24, a user may select therapy parameters for INS 26. The therapy parameters may include an electrode combination, a current or voltage amplitude, a pulse width, and a pulse rate for stimulation signals to be delivered to patient 12. An electrode combination may include a selected subset of one or more electrodes located on implantable leads 18, 20, 22 that are coupled to ICD 16. The electrode combination may also refer to the polarities of the electrodes in the selected subset. By selecting values for amplitude, pulse width, and pulse rate, the physician can attempt to generate an efficacious therapy for patient 12 that is delivered via the selected electrode subset.

In some examples, the user may activate certain features of ICD 16 by entering a single command via programmer 24, such as depression of a single key or combination of keys of a keypad or a single point-and-select action with a pointing device.

As another example, the user may use programmer 24 to retrieve information from INS 26 regarding the performance or integrity of INS 26 or leads 28, 29 (if INS 26 is connected to more than one lead) or a power source of INS 26. With the aid of programmer 24 or another computing device, a user may select values for therapy parameters for controlling therapy delivery by INS 26. The values for the therapy parameters may be organized into a group of parameter values referred to as a "therapy program" or "therapy parameter set." "Therapy program" and "therapy parameter set" are used interchangeably herein.

In the case of electrical stimulation, the therapy parameters for INS 26 may include an electrode combination, and an amplitude, which may be a current or voltage amplitude, and, if INS 26 delivers electrical pulses, a pulse width, and a pulse rate for stimulation signals to be delivered to patient 12. An electrode combination may include a selected subset of one or more electrodes located on implantable lead 28 coupled to INS 26. By selecting particular electrode combinations, a clinician may target particular anatomic structures within patient 12. In addition, by selecting values for amplitude, pulse width, and pulse rate, the physician can attempt to generate an efficacious therapy for patient 12 that is delivered via the selected electrode subset.

Programmer 24 may communicate with ICD 16 and INS 26 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the ICD 16 and INS 26 implant sites in order to improve the quality or security of communication between ICD 16 or INS 26, respectively, and programmer 24.

As described in further detail below, one device, ICD 16 or INS 26, may generate and deliver an electrical signal into adjacent tissue and the other device INS 26 or ICD 16, respectively, may sense the electrical signal. The intradevice electrical signals, i.e., electrical signals generated between electrodes connected to one of ICD 16 or INS 26 and detected by electrodes of the other of the device, may be useful for various purposes, such as facilitating communication between ICD 16 and INS 26 or determining a value of an electrical parameter indicative of impedance of an electrical path between ICD 16 and INS 26. The electrical path may include a path through tissue of patient 12 between the housings of ICD 16 and INS 26, between electrodes electrically connected to the ICD 16 or INS 26 (e.g., between leads 18, 20 or 22 and lead 28) and the housings of INS 26 or ICD 16, respectively, or between electrodes connected to ICD 16 and electrodes connected to INS 26.

The electrical parameter value indicative of the impedance of the electrical path between ICD 16 and INS 26 may be useful for determining an intrathoracic impedance (e.g., the actual impedance value or a value indicative of the impedance) of patient 12. As described in further detail below, intrathoracic impedance may be useful for monitoring a heart-related condition of patient 12, such as heart failure.

In addition, the impedance of the electrical path between ICD 16 and INS 26 may be useful for determining whether a system integrity issue exists. In some example, a system integrity issue may exist if electrodes of leads 18, 20, and/or 22 have moved relative to INS 26 or electrodes of lead 28. Similarly, the impedance of the electrical path between ICD 16 and INS 26 may be useful for determining whether electrodes of lead 28 (and lead 29, if the therapy system includes two leads) have moved relative to ICD 16 or electrodes of leads 18, 20, and/or 22. A system integrity issue may also be present if a lead-related condition exists. A lead-related condition may include, for example, a fractured conductor of the lead, a loose set-screw connecting the lead to the respective device 16, 26, or a change in the electrical insulation separating one or more conductors within the lead.

In some examples, the intradevice electrical signals do not provide any therapeutic benefit to patient 12. In addition, in some examples, the intradevice electrical signals may have a signal characteristic that is less than a threshold required to activate tissue (e.g., a nerve, muscle, etc.) of patient 12, which may help avoid any physiologic response to the intradevice electrical signals that are used to determine interdevice impedance. In some examples, the intensity of the intradevice electrical signals may have a threshold that is less than a perception threshold of patient 12. That is, the intradevice electrical signals generated by ICD 16, e.g., between electrodes of leads 18, 20, 22 or a housing, or generated by INS 26, e.g., between electrodes of lead 28 (and/or lead 29), may be below the threshold of stimulation intensity at which patient 12 senses the stimulation, such that patient 12 does not perceive the transmission of the intradevice electrical signals. An intensity of stimulation may be modified by modifying the current or voltage amplitude of a stimulation signal, a frequency of the stimulation signal, and, if the signal comprises a pulse, a pulse width or pulse shape of the stimulation signal.

A perception threshold or activation threshold may differ between patients. A clinician may determine an activation threshold for a particular nerve of patient 12 based on input from patient 12 or an observable change in physiology. For example, a clinician may increase the intensity of stimulation until patient 12 indicates that paresthesia is present. The intensity at which paresthesia is felt may indicate the activation threshold. In some cases, the activation threshold may include the current or voltage amplitude at which patient 12 experiences paresthesia. As another example, in addition to or instead of the input from patient, the clinician may increase the intensity of stimulation and monitor one or more physiological parameter values until a change is observed. The one or more physiological parameter values may include, for example, heart rate, heart rate variability, cardiovascular pressure, respiration rate, body temperature, and the like. A clinician may determine the perception threshold for patient 12 by delivering test stimulation signals and determining the current or voltage amplitude value (or another stimulation parameter value) at which patient 12 first perceives the stimulation delivered by ICD 16 and/or INS 26.

In other examples, the intradevice electrical signals may have a signal characteristic that is greater than a threshold required to activate tissue (e.g., a nerve, muscle, etc.) of patient 12 or greater than a perception threshold of patient 14. For example, INS 26 may deliver neurostimulation signals to patient 12 to provide therapeutic benefit to patient 12. ICD 16 may sense the neurostimulation signals during these neurostimulation periods in order to determine transthoracic impedance, system integrity (e.g., the placement of ICD 16 and INS 26, and their respective leads, relative to each other).

As previously indicated, in some examples, the intradevice electrical signal generated by one device 16, 26 and sensed by another, separate device 26, 16, may be used to determine an electrical parameter value indicative of an impedance of the electrical path between devices 16, 26. The electrical parameter value indicative of the impedance may be a voltage or current amplitude of the sensed signal or the actual impedance value. For example, based on the voltage or current amplitude of the electrical signal sensed by a device 16 or 26 and the current or voltage amplitude, respectively, of the transmitted signal generated by the other device 26 or 16, at least one of the devices 16 or 26 may determine an impedance of the electrical path between devices 16, 26, such as an electrical path between electrodes of one of leads 18, 20, 22 and/or a housing of ICD 16 and electrodes of lead 28 and/or a housing of INS 26. The impedance of the electrical path between devices 16, 26 may be referred to as an interdevice impedance. In some cases, the interdevice impedance may be indicative of the transthoracic impedance of patient 12.

In some examples, ICD 16 may generate and deliver an electrical signal between two or more electrodes on one or more of leads 18, 20, 22 or on a housing of ICD 16, and INS 26 may sense the electrical signal via two or more sense electrodes of lead 28 or a housing of INS 26. In other examples, INS 26 may generate and deliver an electrical signal between two or more electrodes on lead 28 and/or a housing of INS 26, and ICD 16 may sense the electrical signal via two or more sense electrodes of one or more leads 18, 20, 22 and/or a housing of ICD 16.

The impedance of the electrical path between devices 16, 26 may change over the life of therapy system 10, e.g., as leads 18, 20, 22, ICD 16, lead 28, or INS 26 move within patient 12 and the amount of tissue or characteristics of tissue between devices 16, 26 and associated leads change. In some cases, the impedance of the electrical path between devices 16, 26 may change over time as the impedance of an electrical path between ICD 16 and electrodes of leads 18, 20, and/or 22 changes, or as the impedance of an electrical path between electrodes of lead 28 and INS 26 changes. The impedance of the various electrical paths between devices 16, 26 and the respective leads may vary over the life of ICD 16 and INS 28 due to, for example, material degradation of the leads 18, 20, 22, 28 or tissue growth proximate to one or more electrodes of the lead. Further, one or more leads 18, 20, 22, and/or 28 may develop a short between two or more conductors due to a lead-related condition, e.g., when insulation is compromised, or when a conductor fractures due to bending or other stresses placed on the lead by patient movement or manipulation.

Changes in an impedance of the electrical path between ICD 16 and INS 26 may indicate that ICD 16, INS 26 or one of the associated leads 18, 20, 22, and 28 have moved relative to each other or that a lead-related condition may be present. Thus, the change in the interdevice impedance may indicate a change in the ability of ICD 16 or INS 26 to effectively sense electrical cardiac activity and/or deliver stimulation to a desired stimulation site. Movement of leads 18, 20, 22, 28 or the housings of devices 16, 26 may be undesirable. For example, with respect to the vagus nerve stimulation example shown in FIG. 1, migration of lead 28 or INS 26 may cause displacement of electrodes by lead 28 with respect to target stimulation site 40. In such a situation, the electrodes may not be properly positioned to deliver therapy to target stimulation site 40, resulting in reduced electrical coupling, and possibly undermining therapeutic efficacy of the neurostimulation therapy from INS 26.

In addition, if electrodes of lead 28 migrated toward heart 14, the relatively high frequency neurostimulation (e.g., 50 Hz or greater) delivered by INS 26 may capture heart 14 and pace heart 14, which may induce an arrhythmia. In some examples, if migration of one or more of the leads 18, 20, 22, 28 is detected, ICD 16 or INS 26 may generate an integrity indication and, in some cases, change therapy parameter values or suspend therapy delivery to patient 14. For at least these reasons, it may be desirable to identify changes in the interdevice impedance in order to take corrective action, such as implantation of a new lead, selection of different electrodes for sensing or delivery of stimulation, surgery to relocate ICD 16 or INS 26 or modifying one or more stimulation parameter values. In some examples described herein, at least one of ICD 16 or INS 26 may determine an electrical parameter value indicative of interdevice impedance to determine whether a lead position has changed or whether a lead integrity issue may be present.

The impedance of the electrical path between ICD 16 and INS 26 may also change as a result of physiological changes in patient 12. For example, interdevice impedance of an electrical path that extends across the patient's chest may be indicative of the fluid status of patient 12 as it relates to the patient's health. As described in further detail below, the electrical parameter value indicative of interdevice impedance may be used to determine an electrical parameter value indicative of a transthoracic impedance (which may also be referred to as intrathoracic impedance) of patient 12 because the signal used to determine the impedance or other electrical parameter value indicative of the impedance is transmitted across the patient's thorax. Interdevice impedance and transthoracic impedance are used interchangeably, although transthoracic impedance depends upon the relative implant sites of ICD 16 and INS 26. The electrical parameter value indicative of interdevice impedance may be an impedance value or a current or voltage amplitude of a signal sensed by the non-transmitting device.

The electrical parameter value indicative of transthoracic impedance of patient 12 may be used to monitor the cardiac function of patient 12 because fluid status may be indicative of the patient's health. Accumulation of fluid may indicate exacerbation of heart failure or another condition that affects cardiac activity, such as left-sided myocardial infarction, high blood pressure, altitude sickness, emphysema, renal disease, and the like. Decreases in transthoracic impedance may indicate an increase in fluid content in the patient's thorax, and increases in transthoracic impedance may indicate a decrease in fluid content. ICD 16 and/or INS 26 may monitor interdevice impedance values in order to generate data indicative of the patient's health. This data may be reviewed by a clinician and/or used by ICD 16 and INS 26 to control therapy delivery to patient 14.

An electrical parameter value indicative of transthoracic impedance may be used to determine how much fluid is present in the patient's thorax, which may be used to detect or predict congestive heart failure, pulmonary edema, pleural effusion, increased blood volume, hypertension/hypotension or other patient conditions. Fluid build-up in the patient's thoracic region, e.g., due to edema, may result in a change in impedance of the electrical path between ICD 16 and INS 26. Edema may be a result of heart failure, e.g., congestive heart failure. Decreases in transthoracic impedance may indicate increases in fluid content within the patient's thorax and increases in transthoracic impedance may indicate decreases in fluid content.

The transthoracic impedance may also be used to determine respiration activity of patient 12. The respiration activity, e.g., a respiration rate, of patient 12 may be used to control the delivery of pacing pulses to heart 14 of patient 12 by ICD 16. As an example, a higher respiration rate as indicated by a change in thoracic impedance may indicate that patient 12 is exercising, and, thus, it may be desirable for ICD 16 to deliver pacing pulses to heart 14 at a faster rate. The transthoracic impedance may also be used to determine stroke volume of a cardiac contraction, which may be useful to monitor heart failure or to determine the presence of ventricular fibrillation.

The impedance of the electrical path between ICD 16 and INS 26 may be affected by physiological changes in patient 12 that may or may not be directly related to the patient's health. For example, the impedance may change based on the hydration level of patient 12 or the amount of salt consumed by patient, which may affect the amount of fluid retained within tissue, and, therefore, the conductivity of the patient's tissue. As another example, posture changes of patient 12 may shift the fluid within the patient's body, which may also affect the impedance of the electrical path between devices 16, 26. In some examples, accelerometers may be used to determine position or posture of patient 14, and different patient positions or postures may be associated with a threshold impedance value, e.g., an impedance value that indicates patient 12 is in an acceptable physiological condition or that a system integrity issue is not present, as indicated by fluid status (e.g., fluid within the thorax). An acceptable physiological condition may include, for example, a low level of fluid present in the patient's lungs.

Due to the effect of physiological changes in patient 12 on an impedance of the electrical path between ICD 16 and INS 26, a range of interdevice impedance values may be considered acceptable. As described below with respect to FIG. 10, a range of interdevice impedance values may indicate that ICD 16, INS 26 or the respective leads 18, 20, 22, 28 have not moved relative to each other or are within an acceptable distance range of each other, e.g., a range of distances that does not adversely affect the efficacy of therapy delivery. On the other hand, an interdevice impedance value that is outside of the acceptable range of values may indicate that the interdevice impedance has changed and corrective action, e.g., repositioning ICD 16, INS 26 or the respective leads, modifying therapy parameter values, and so forth, may be desirable.

In some examples, a trend, such as a rate of change, of interdevice impedance values over time may indicate whether a the impedance of the electrical path between ICD 16 and INS 26 is attributable to a physiologic change within patient 12 or a therapy system integrity issue. A therapy system integrity issue may include circumstances in which at least one of the leads 18, 20, 22, 28, 29 have moved within patient 12 or moved relative to each other or ICD 16 or ICD 16. A therapy system integrity issue may also include circumstances in which at least one housings if ICD 16 or INS 26 have moved within patient 12 or moved relative to each other or a lead 18, 20, 22, 28, 29. In addition, a therapy system integrity issue may include circumstances in which at least one of the leads 18, 20, 22, 28, 29 exhibits a lead-related condition, such as a change in the structure of the lead (e.g., a fractured conductor, loose set-screw connecting the lead to the respective device 16, 26, or a change in the electrical insulation).

Physiologic changes that may affect intrathoracic impedance may take place over a known time course. For example, changes in transthoracic impedance due to congestive heart failure may take place over the course of a few days. Accordingly, a rate of change of intrathoracic impedance values that exceed a threshold of change may be indicative of system integrity issue (e.g., a lead-related condition) or changes to the patient's posture or activity level. In this way, the rate of change of electrical parameter values indicative of intrathoracic impedance over time may be indicative of a cause of the change in the intrathoracic impedance. In some examples, in order to detect a patient condition that may require additional clinician attention, ICD 16 and/or INS 26 may compare a determined intrathoracic impedance to a threshold value or determine whether the intrathoracic impedance has changed by a threshold percentage relative to a threshold value that is based on prior-determined intrathoracic impedances. The threshold value may be, for example, a mean, median or another value of the determined intrathoracic impedances for a particular range of time preceding the current time. In this way, the threshold value may be a moving threshold. In addition, the determined intrathoracic impedance that is compared to the threshold value may be a mean or median intrathoracic impedance over a certain period of time or an intrathoracic impedance at a discrete point in time.

In some examples, ICD 16 may transmit an electrical signal across two or more electrodes coupled to ICD 16, and INS 26 may sense the electrical signal. Accordingly, in some examples, therapy system 10 may utilize a quadrapolar electrode configuration to determine transthoracic impedance. For example, ICD 16 may transmit an electrical signal across two electrodes and INS 26 may sense the electrical signal using two separate electrodes. Because ICD 16 and INS 26 are implanted in separate locations within the body of patient 12, INS 26 may sense an electrical signal that has transmitted across the patient's thorax. In this way, when INS 26 determines the resulting voltage or current of the sensed signal, the impedance of the patient's thorax may be determined. The impedance or the resulting voltage or current of the sensed signal may be stored in a memory of ICD 16, INS 26, programmer 24 or another device as an electrical parameter value indicative of the transthoracic impedance. In other examples, INS 26 may transmit an electrical signal using two or more electrodes coupled to INS 26 and ICD 16 may sense the electrical signal.

System 10 (FIGS. 1 or 2) including two devices 16, 26 may provide a better indication of the patient's transthoracic impedance compared to systems in which thoracic impedance is determined via electrodes of a single device because, with system 10, the electrical signal may be transmitted across a greater percentage of the patient's thorax. As a result, a better indication of pulmonary edema or thoracic congestion may be generated based on the intrathoracic impedance determinations. Depending on the sites at which ICD 16 and INS 26 are implanted, the vector between ICD 16 and INS 26, and the associated leads 18, 20, 22, 28, 29, may better capture the thoracic region of patient 12. In addition, an electrical signal that is generated by one of the devices 16, 26 may generate an electrical field that is sensed across the thoracic region by the other device 26, 16, respectively. In contrast, a single IMD that determines intrathoracic region may capture a smaller region of the patient's thoracic region, which may be limited by the size of the leads that are coupled to the IMD and carry electrodes that are used for determining the intrathoracic impedance.

Therapy system 10 may determine the electrical parameter value indicative of the transthoracic impedance based on the sensed electrical signal, i.e., the electrical signal that is modulated by fluid in the tissue between devices 16, 26, and/or leads 18, 20, 22, 28, 29. In addition, the use of two devices 16, 26 comprising respective leads 18, 20, 22, 28 may increase the number of electrode combinations that may be used to generate and deliver the electrical signal that is used to determine the transthoracic impedance.

The intradevice electrical signals that are transmitted between electrodes of ICD 16 may also be used to transmit information between ICD 16 and INS 26. For example, INS 26 may sense electrical communication signals generated by ICD 16 and demodulate the signal to extract information from the signals. The electrical communication signals may have an intensity that is less than an activation threshold of tissue of patient 12, such that the electrical communication signals substantially do not provoke a physiological response by the patient's tissue. As another example, ICD 16 may sense the electrical communication signals generated by INS 26 and demodulate the signal to extract information from the signals. Information that is transmitted between ICD 16 and INS 26 via the electrical communication signals may include, for example, operating instructions for INS 26, therapy parameter values, the voltage or current amplitude of an intradevice signal generated by the device for purposes of determining interdevice impedance, and the like. Similarly, electrical signals that are transmitted between electrodes of INS 26 may also be used to transmit information from INS 26 to ICD 16. ICD 16 may sense the electrical signals and demodulate the signal to extract information from the signals.

Figure 3:
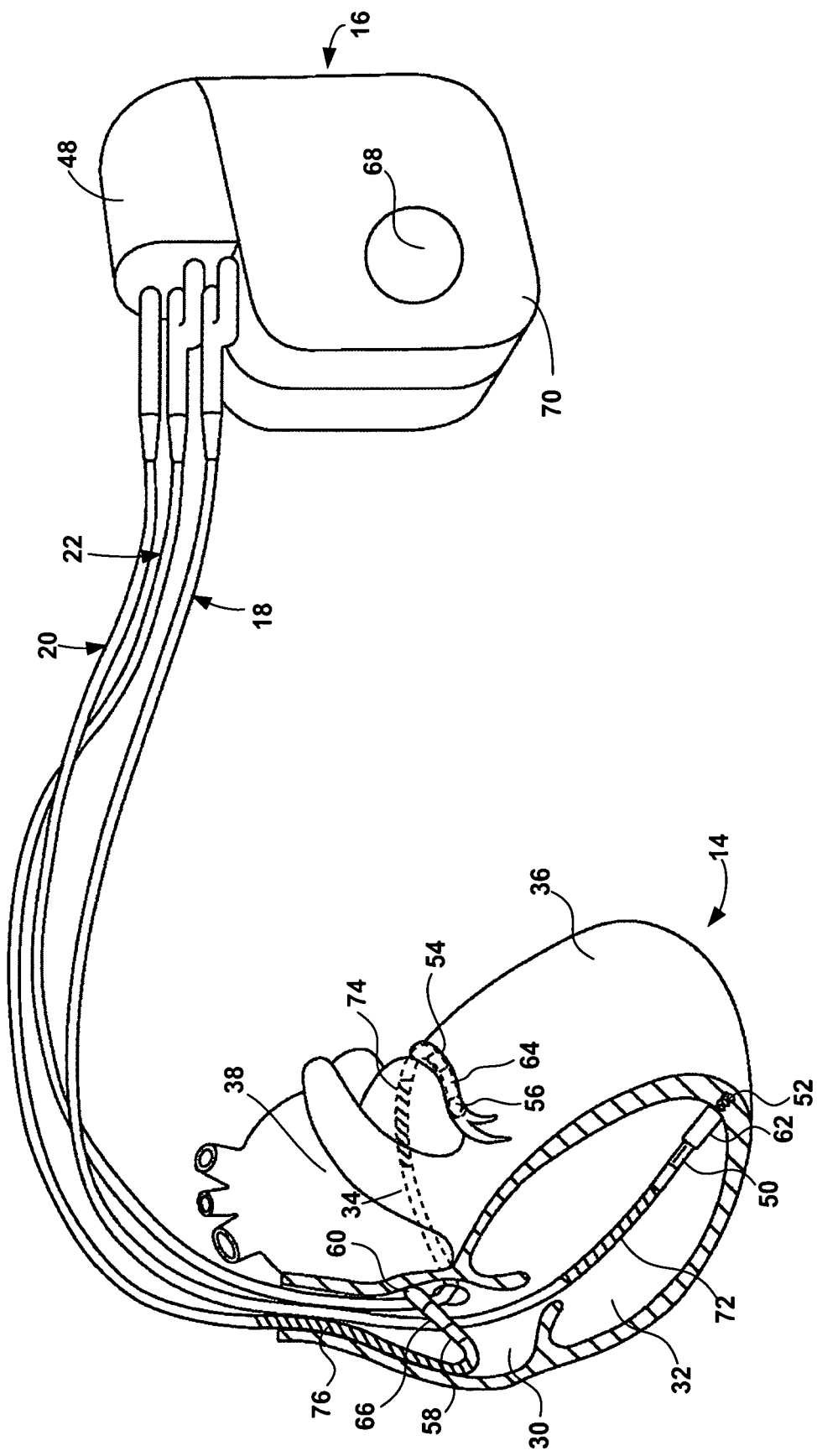
FIG. 3 is a conceptual diagram illustrating the ICD and associated leads of the therapy systems of FIGS. 1 and 2 in greater detail.

FIG. 3 is a conceptual diagram illustrating ICD 16 and leads 18, 20, 22 of therapy system 10 in greater detail. Leads 18, 20, 22 may be electrically coupled to a signal generator, a sensing module, or other modules ICD 16 via connector block 48. In some examples, proximal ends of leads 18, 20, 22 may include electrical contacts that electrically couple to respective electrical contacts within connector block 48. In addition, in some examples, leads 18, 20, 22 may be mechanically coupled to connector block 48 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. Other lead configurations are also contemplated, such as leads that do not include coiled conductors. In the illustrated example, bipolar electrodes 50 and 52 are located proximate to a distal end of lead 18. In addition, bipolar electrodes 54 and 56 are located proximate to a distal end of lead 20 and bipolar electrodes 58 and 60 are located proximate to a distal end of lead 22.

Electrodes 50, 54 and 58 may take the form of ring electrodes, and electrodes 52, 56 and 60 may take the form of extendable helix tip electrodes mounted retractably within insulative electrode heads 62, 64, and 66, respectively. Each of the electrodes 50, 52, 54, 56, 58, and 60 may be electrically coupled to a respective one of the conductors within the lead body of its associated lead 18, 20, 22, and thereby coupled to respective ones of the electrical contacts on the proximal end of leads 18, 20 and 22.

Electrodes 50, 52, 54, 56, 58, and 60 may sense electrical signals attendant to the depolarization and repolarization of heart 14. The electrical signals are conducted to ICD 16 via the respective leads 18, 20, 22. In some examples, ICD 16 also delivers pacing pulses via electrodes 50, 52, 54, 56, 58, and 60 to cause depolarization of cardiac tissue of heart 14. In some examples, as illustrated in FIG. 2, ICD 16 includes one or more housing electrodes, such as housing electrode 68, which may be formed integrally with an outer surface of hermetically-sealed housing 70 of ICD 16 or otherwise coupled to housing 70. In some examples, housing electrode 68 is defined by an uninsulated portion of an outward facing portion of housing 70 of ICD 16. Other division between insulated and uninsulated portions of housing 70 may be employed to define two or more housing electrodes. In some examples, housing electrode 68 comprises substantially all of housing 70. Any of the electrodes 50, 52, 54, 56, 58, and 60 may be used for unipolar sensing or pacing in combination with housing electrode 68. As described in further detail with reference to FIG. 4, housing 70 may enclose a signal generator that generates cardiac pacing pulses and defibrillation or cardioversion shocks, as well as a sensing module for monitoring the patient's heart rhythm.

Leads 18, 20, 22 also include elongated electrodes 72, 74, 76, respectively, which may take the form of a coil. ICD 16 may deliver defibrillation pulses to heart 14 via any combination of elongated electrodes 72, 74, 76, and housing electrode 68. Electrodes 68, 72, 74, 76 may also be used to deliver cardioversion pulses to heart 14. Electrodes 72, 74, 76 may be fabricated from any suitable electrically conductive material, such as, but not limited to, platinum, platinum alloy or other materials known to be usable in implantable defibrillation electrodes. In other examples, elongated electrodes 72, 76 may be located on lead 18 and leads 20, 22 may not include any electrodes. Other configurations of leads 18, 20, 22, and their respective electrodes are contemplated.

The configuration of therapy system 10 illustrated in FIGS. 1-3 are merely examples. In other examples, a therapy system may include epicardial leads and/or patch electrodes instead of or in addition to the transvenous leads 18, 20, 22 illustrated in FIG. 1. Further, ICD 16 and INS 26 need not be implanted within patient 12. In examples in which ICD 16 is not implanted in patient 12, ICD 16 may deliver defibrillation pulses and other therapies to heart 14 via percutaneous leads that extend through the skin of patient 12 to a variety of positions within or outside of heart 14. In examples in which INS 26 is not implanted in patient 12, INS 26 may deliver electrical stimulation to target tissue sites within patient 12 or sense ICD stimulation within patient 12 via external electrodes or via percutaneous leads that extend through the skin of patient 12.

In other examples of therapy systems that provide electrical stimulation therapy to heart 14, a therapy system may include any suitable number of leads coupled to ICD 16, and each of the leads may extend to any location within or proximate to heart 14. For example, other examples of therapy systems may include three transvenous leads located as illustrated in FIGS. 1 and 3, and an additional lead located within or proximate to left atrium 38. As another example, other examples of therapy systems may include a single lead that extends from ICD 16 into right atrium 30 or right ventricle 32, or two leads that extend into a respective one of the right ventricle 32 and right atrium 30. An example of this type of therapy system is shown in FIG. 4.

Figure 4:
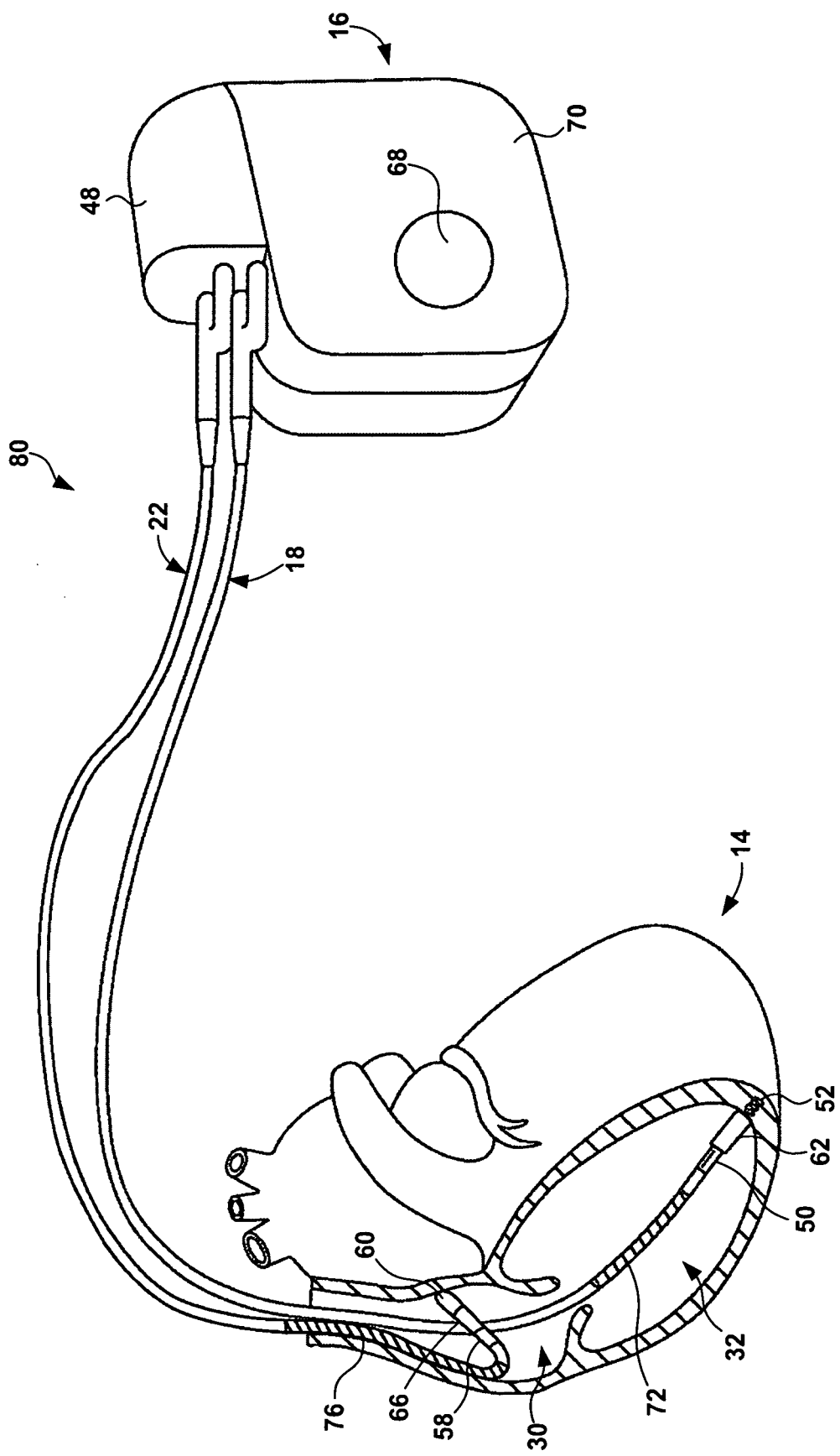
FIG. 4 is a conceptual diagram illustrating another example ICD lead configuration.

FIG. 4 is a conceptual diagram illustrating another example of therapy system 80, which is similar to therapy system 10 of FIGS. 1-2, but includes two leads 18, 22, rather than three leads. Leads 18, 22 are implanted within right ventricle 32 and right atrium 30, respectively. Therapy system 80 shown in FIG. 4 may be useful for providing defibrillation and pacing pulses to heart 14. Therapy system 80 may further include INS 26 (not shown in FIG. 4), which is configured to deliver electrical stimulation therapy to one or more nerves or spinal cord 44 (FIG. 2) of patient 12 in order to help prevent or mitigate an arrhythmia of patient 12.

Figure 5:
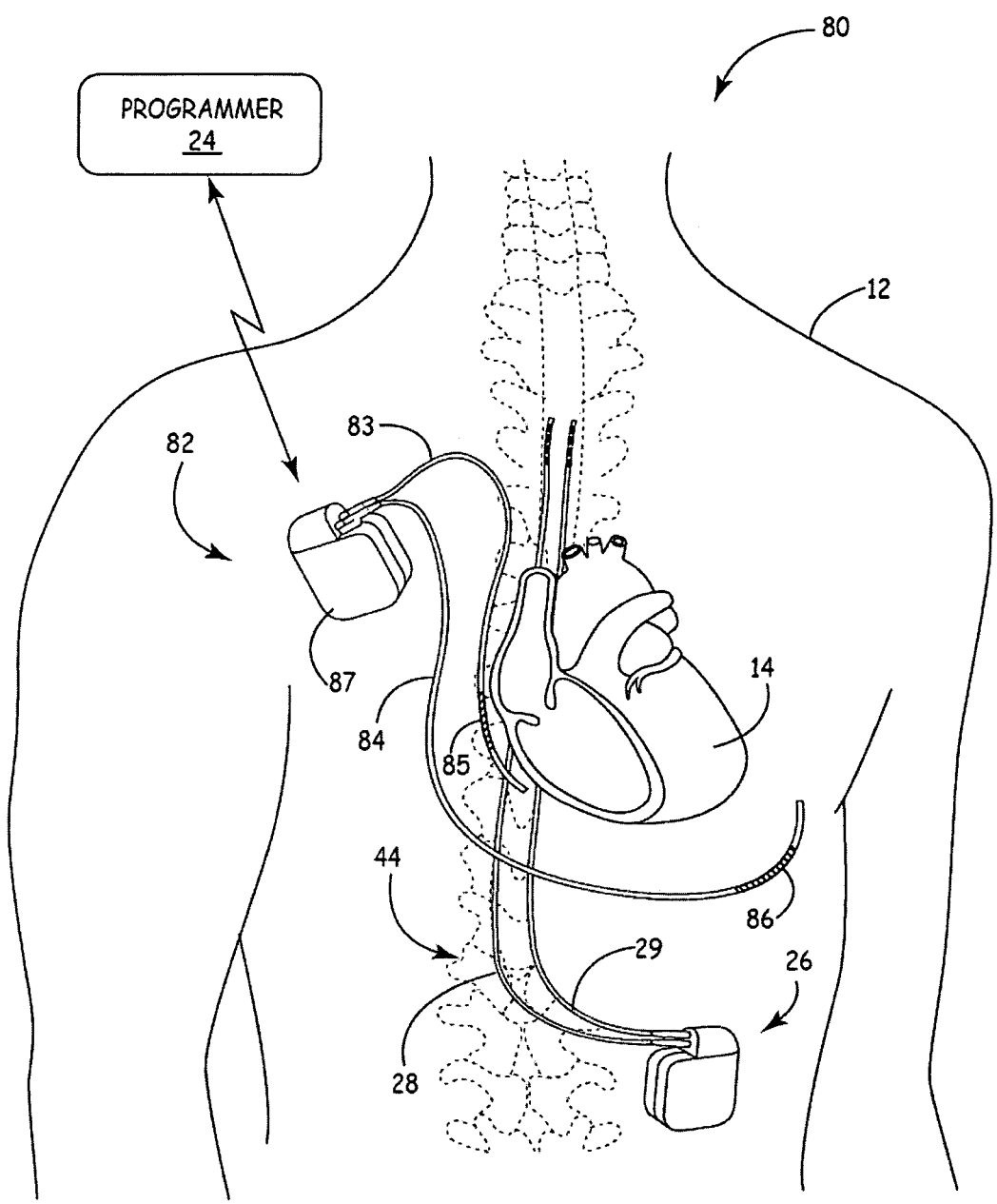
FIG. 5 is a conceptual diagram illustrating another example therapy system that includes an ICD and an INS.

FIG. 5 is a conceptual diagram of another example therapy system 81 that includes two medical devices to provide therapy to patient 12. In addition to INS 26, therapy system 81 includes ICD 82, which delivers electrical stimulation to heart 14 without intravascular leads. ICD 82 is coupled to extravascular leads 83, 84, which each include at least one electrode 85, 86, respectively. Electrodes 85, 86 may be subcutaneous coil electrodes, which may be positioned within a subcutaneous tissue layer of patient 12. In other examples, electrodes 85, 86 may comprise any other suitable type of extravascular electrode. For example, electrodes 85, 86 may include any other type of subcutaneous electrode, such as subcutaneous ring electrodes, subcutaneous plate electrodes, subcutaneous patch or pad electrodes, or any other type of extrathoracic electrode, such as a submuscular electrode, an epicardial electrode or an intramural electrode.

Electrodes 85 may be located within the thoracic cavity of patient 12 proximate to right ventricle 32 (FIG. 1), on the patient's side or back, or any other portion of the body appropriate for providing electrical stimulation to heart 14. Electrode 86 may be located within the thoracic cavity of patient 12 proximate left ventricle 36 (FIG. 1), on the patient's side or back, or any other portion of the body appropriate for providing electrical stimulation to the heart. Similar extravascular electrodes are disclosed in commonly-assigned U.S. Pat. No. 5,261,400 to Bardy, which is entitled "DEFIBRILLATOR EMPLOYING TRANSVENOUS AND SUBCUTANEOUS ELECTRODES AND METHOD OF USE" and issued Nov. 16, 1993, and U.S. Pat. No. 5,292,338 to Bardy, which is entitled "ATRIAL DEFIBRILLATOR EMPLOYING TRANSVENOUS AND SUBCUTANEOUS ELECTRODES AND METHOD OF USE" and issued Mar. 8, 1994. U.S. Pat. Nos. 5,261,400 and 5,292,338 are incorporated herein by reference in their entireties.

Leads 83, 84 may be electrically coupled to stimulation modules, and, in some cases, sensing modules, that are enclosed within housing 87 of ICD 82. As with housing 70 of ICD 16 (FIG. 3), housing 87 may comprise a hermetic housing that substantially encloses the components of ICD 16, such as a sensing module, stimulation generator, processor and the like. Components of an example ICD 16 or ICD 82 are described with respect to FIG. 6. ICD 82 may deliver electrical stimulation (e.g., pacing, cardioversion or defibrillation pulses) to heart 14 between electrodes 85, 86 e.g., in a bipolar configuration. In other examples, ICD 82 may deliver electrical stimulation to heart 14 between electrodes 85 and housing 87 (or an electrode attached to an outer surface of housing 87), or between electrode 86 and housing 87, e.g., in a unipolar configuration.

Just as with therapy system 10 (FIG. 1) an impedance of an electrical path between ICD 82 and INS 26, between electrodes of leads 28, 29 and electrodes of leads 83, 84, between electrodes of leads 28, 29 and ICD 82, or between electrodes of leads 82, 84 and INS 26 may be determined using the techniques described herein. Accordingly, while the disclosure primarily refers to therapy system 10 including ICD 16 (FIG. 1) and INS 26, the description of the techniques, systems, and devices herein are also applicable to therapy system 90 including ICD 82 and INS 26.

FIG. 6 is a functional block diagram of an example configuration of ICD 16, which includes processor 90, memory 92, signal generator 94, sensing module 96, telemetry module 98, and power source 100. Memory 92 includes computer-readable instructions that, when executed by processor 90, cause ICD 16 and processor 90 to perform various functions attributed to ICD 16 and processor 90 herein. Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 90 may include any one or more of a microprocessor, a controller, a digital signal processor (DSP), an application specific integrated circuit (ASIC), a field-programmable gate array (FPGA), or equivalent discrete or integrated logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof. Processor 90 controls signal generator 94 to deliver stimulation therapy to heart 14 according to a selected one or more of therapy programs, which may be stored in memory 92. Specifically, processor 44 may control signal generator 94 to deliver electrical pulses with the amplitudes, pulse widths, frequency, or electrode polarities specified by the selected one or more therapy programs.

Signal generator 94 is electrically coupled to electrodes 50, 52, 54, 56, 58, 60, 68, 72, 74, and 76, e.g., via conductors of the respective lead 18, 20, 22, or, in the case of housing electrode 68, via an electrical conductor disposed within housing 70 of ICD 16. Signal generator 94 is configured to generate and deliver electrical stimulation therapy to heart 14. For example, signal generator 94 may deliver defibrillation shocks to heart 14 via at least two of electrodes 68, 72, 74, 76. Signal generator 94 may deliver pacing pulses via ring electrodes 50, 54, 58 coupled to leads 18, 20, and 22, respectively, and/or helical electrodes 52, 56, and 60 of leads 18, 20, and 22, respectively. In some examples, signal generator 94 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 94 may include a switch module and processor 90 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes. In other examples, however, signal generator 94 may independently deliver stimulation to electrodes 50, 52, 54, 56, 58, 60, 68, 72, 74, and 76, or selectively sense via one or more of electrodes 50, 52, 54, 56, 58, 60, 68, 72, 74, and 76, without a switch matrix.

As described in further detail below, signal generator 94 may also generate an electrical signal between two or more electrodes 50, 52, 54, 56, 58, 60, 68, 72, 74, and 76 in order to determine an electrical parameter value indicative of an impedance of an electrical path between ICD 16 and INS 26 or to generate nontherapeutic signals for communicating with INS 26.

Sensing module 96 monitors signals from at least one of electrodes 50, 52, 54, 56, 58, 60, 68, 72, 74, and 76 in order to monitor electrical activity of heart 14, e.g., via EGM and/or electrocardiogram (ECG) signals. Sensing module 96 may also include a switch module to select which of the available electrodes are used to sense the heart activity. In some examples, processor 90 may select the electrodes that function as sense electrodes via the switch module within sensing module 96, e.g., by providing signals via a data/address bus. In some examples, sensing module 96 includes one or more sensing channels, each of which may comprise an amplifier. In response to the signals from processor 90, the switch module of within sensing module 96 may couple the outputs from the selected electrodes to one of the sensing channels.

In some examples, one channel of sensing module 96 may include an R-wave amplifier that receives signals from electrodes 50 and 52, which are used for pacing and sensing in right ventricle 32 of heart 14. Another channel may include another R-wave amplifier that receives signals from electrodes 54 and 56, which are used for pacing and sensing proximate to left ventricle 36 of heart 14. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 96 may include a P-wave amplifier that receives signals from electrodes 58 and 60, which are used for pacing and sensing in right atrium 30 of heart 14. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 96 may be selectively coupled to housing electrode 68, or elongated electrodes 72, 74, or 76, with or instead of one or more of electrodes 50, 52, 54, 56, 58 or 60, e.g., for unipolar sensing of R-waves or P-waves in any of chambers 30, 32, or 36 of heart 14.

In some examples, sensing module 96 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 92 as an electrogram (EGM). In some examples, the storage of such EGMs in memory 92 may be under the control of a direct memory access circuit. Processor 90 may employ digital signal analysis techniques to characterize the digitized signals stored in memory 92 to detect and classify the patient's heart rhythm from the electrical signals. Processor 90 may detect and classify the heart rhythm of patient 12 by employing any of the numerous signal processing methodologies known in the art.

Sensing module 96 is also configured to collect, determine and/or calculate impedance data for any of a variety of electrical paths that include two or more of electrodes 50, 52, 54, 56, 58, 60, 68, 72, 74, and 76. In addition, in some examples, sensing module 96 is configured to collect, determine, and/or calculate impedance data for an impedance path between two or more electrodes 50, 52, 54, 56, 58, 60, 68, 72, 74, and 76 of ICD 16 and one or more electrodes of lead 28, which is coupled to INS 26, or the INS housing, as described in further detail below with reference to FIG. 9. For example, sensing module 96 may sense an electrical signal that is generated between two electrodes of lead 28, which is coupled to INS 26, and determine an impedance value or other electrical parameter value that indicates the impedance of the electrical path through tissue between ICD 16 and INS 26. Sensing module 96 may sense the intradevice signal generated by INS 26 via a wide band channel, transmit the sensed signal through an analog-to-digital converter, and then digitally process the signal with processor 90 to determine a transthoracic impedance or to extract information communicated by INS 26 via the sensed signal.

If ICD 16 is configured to generate and deliver pacing pulses to heart 14, processor 90 may include pacer timing and control module, which may be embodied as hardware, firmware, software, or any combination thereof. The pacer timing and control module may comprise a dedicated hardware circuit, such as an ASIC, separate from other processor 90 components, such as a microprocessor, or a software module executed by a component of processor 90, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided. When a pacing code includes "D" as the third letter in the code, it may indicate that the sensed signal is used for tracking purposes.

Intervals defined by the pacer timing and control module within processor 90 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from sensing module 96 to blank one or more channels, e.g., amplifiers, for a period during and after delivery of electrical stimulation to heart 14. The durations of these intervals may be determined by processor 90 in response to stored data in memory 92. The pacer timing and control module of processor 90 may also determine the amplitude of the cardiac pacing pulses.

During pacing, escape interval counters within the pacer timing/control module of processor 90 may be reset upon sensing of R-waves and P-waves. Signal generator 94 may include pacer output circuits that are coupled, e.g., selectively by a switching module, to any combination of electrodes 50, 52, 54, 56, 58, 60, 68, 72, 74, and 76 appropriate for delivery of a bipolar or unipolar pacing pulse to one of the chambers of heart 14. Processor 90 may reset the escape interval counters upon the generation of pacing pulses by signal generator 94, and thereby control the basic timing of cardiac pacing functions, including anti-tachyarrhythmia pacing.

The value of the count present in the escape interval counters when reset by sensed R-waves and P-waves may be used by processor 90 to determine the durations of R-R intervals, P-P intervals, P-R intervals and R-P intervals, which are measurements that may be stored in memory 92. Processor 90 may use the count in the interval counters to detect a tachyarrhythmia event, such as ventricular fibrillation event or ventricular tachycardia event. Upon detecting a threshold number of tachyarrhythmia events, processor 90 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode. In the case of a NST, however, processor 90 may not meet the requirements for triggering a therapeutic response.

In some examples, processor 90 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 90 and any updating of the values or intervals controlled by the pacer timing and control module of processor 90 may take place following such interrupts. A portion of memory 92 may be configured as a plurality of recirculating buffers, capable of holding series of measured intervals, which may be analyzed by processor 90 in response to the occurrence of a pace or sense interrupt to determine whether heart 14 of patient 12 is presently exhibiting atrial or ventricular tachyarrhythmia.

In some examples, an arrhythmia detection method may include any suitable tachyarrhythmia detection algorithms. In one example, processor 90 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 90 in other examples.

In the examples described herein, processor 90 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 92 of ICD 16. In addition, the number of tachyarrhythmia events that are detected to confirm the presence of a tachyarrhythmia episode may be stored as a number of intervals to detect (NID) threshold value in memory 92. In some examples, processor 90 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, processor 90 may determine that the tachyarrhythmia is present.

If processor 90 detects an atrial or ventricular tachyarrhythmia based on signals from sensing module 96, and an anti-tachyarrhythmia pacing regimen is desired, timing intervals for controlling the generation of anti-tachyarrhythmia pacing therapies by signal generator 94 may be loaded by processor 90 into the pacer timing and control module to control the operation of the escape interval counters therein and to define refractory periods during which detection of R-waves and P-waves is ineffective to restart the escape interval counters.

If ICD 16 is configured to generate and deliver defibrillation pulses to heart 14, signal generator 94 may include a high voltage charge circuit and a high voltage output circuit. In the event that generation of a cardioversion or defibrillation pulse is required, processor 90 may employ the escape interval counter to control timing of such cardioversion and defibrillation pulses, as well as associated refractory periods. In response to the detection of atrial or ventricular fibrillation or tachyarrhythmia requiring a cardioversion pulse, processor 90 may activate a cardioversion/defibrillation control module, which may, like pacer timing and control module, be a hardware component of processor 90 and/or a firmware or software module executed by one or more hardware components of processor 90. The cardioversion/defibrillation control module may initiate charging of the high voltage capacitors of the high voltage charge circuit of signal generator 94 under control of a high voltage charging control line.

Processor 90 may monitor the voltage on the high voltage capacitor, e.g., via a voltage charging and potential (VCAP) line. In response to the voltage on the high voltage capacitor reaching a predetermined value set by processor 90, processor 90 may generate a logic signal that terminates charging. Thereafter, timing of the delivery of the defibrillation or cardioversion pulse by signal generator 94 is controlled by the cardioversion/defibrillation control module of processor 90. Following delivery of the fibrillation or tachycardia therapy, processor 90 may return signal generator 94 to a cardiac pacing function and await the next successive interrupt due to pacing or the occurrence of a sensed atrial or ventricular depolarization.

Signal generator 94 may deliver cardioversion or defibrillation pulses with the aid of an output circuit that determines whether a monophasic or biphasic pulse is delivered, whether housing electrode 68 serves as cathode or anode, and which electrodes are involved in delivery of the cardioversion or defibrillation pulses. Such functionality may be provided by one or more switches or a switching module of signal generator 94.

Telemetry module 98 includes any suitable hardware, firmware, software or any combination thereof for communicating with another device, such as programmer 24 (FIG. 1). Under the control of processor 90, telemetry module 98 may receive downlink telemetry from and send uplink telemetry to programmer 24 with the aid of an antenna, which may be internal and/or external. Processor 90 may provide the data to be uplinked to programmer 24 and the control signals for the telemetry circuit within telemetry module 98, e.g., via an address/data bus. In some examples, telemetry module 98 may provide received data to processor 90 via a multiplexer.

In some examples, processor 90 may transmit atrial and ventricular heart signals (e.g., ECG signals) produced by atrial and ventricular sense amp circuits within sensing module 96 to programmer 24. The atrial and ventricular heart signals, as well as other physiological parameters of patient 12 sensed by ICD 16 may be transmitted to programmer 24 or another device for diagnostic purposes, e.g., to diagnose a severity of the patient's condition. Programmer 24 may interrogate ICD 16 to receive the heart signals. Processor 90 may store heart signals within memory 92, and retrieve stored heart signals from memory 92. Processor 90 may also generate and store marker codes indicative of different cardiac episodes that sensing module 96 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of ICD 16 are coupled to power source 100, which may include a rechargeable or non-rechargeable battery. A non-rechargeable battery may be selected to last for several years, while a rechargeable battery may be inductively charged from an external device, e.g., on a daily or weekly basis.

In some examples, data from sensing module 96 may be uploaded to a remote server, from which a clinician or another user may access the data to determine whether a potential sensing integrity issue exists or whether the determined electrical parameter value indicative of transthoracic impedance of patient 12 indicates patient 12 requires medical attention. An example of a remote server includes the CareLink Network, available from Medtronic, Inc. of Minneapolis, Minn. An example of a system that includes an external device, such as a server, and one or more computing devices that are coupled to ICD 16 and programmer 24 via a network is described below with respect to FIG. 13.

FIG. 7 is a functional block diagram of an example INS 26. INS 26 includes processor 110, memory 112, signal generator 114, sensing module 115, switching module 116, telemetry module 118, and power source 120. In the example shown in FIG. 7, processor 110, memory 112, signal generator 114, switching module 116, telemetry module 118, and power source 120 are enclosed within housing 122, which may be, for example a hermetic housing. As shown in FIG. 7, signal generator 114 is coupled to lead 28 either directly or indirectly (e.g., via a lead extension). Alternatively, signal generator 114 may be coupled more than one lead directly or indirectly (e.g., via a lead extension, such as a bifurcating lead extension that may electrically and mechanically couple to two leads) as needed to provide neurostimulation therapy to patient 12.

In the example illustrated in FIG. 7, lead 28 includes electrodes 124A-124D (collectively referred to as "electrodes 124"). Electrodes 124 may comprise ring electrodes. In other examples, electrodes 124 may be arranged in a complex electrode array that includes multiple non-contiguous electrodes at different angular positions about the outer circumference of lead 28, as well as different levels of electrodes spaced along a longitudinal axis of lead 28. The configuration, type, and number of electrodes 124 illustrated in FIG. 7 are merely exemplary. In other examples, INS 26 may be coupled to any suitable number of leads with any suitable number and configuration of electrodes. Moreover, lead 28 may comprise a shape other than a cylindrical shape. As an example, lead 28 may comprise a paddle-shaped portion that carries electrodes 124.

Memory 112 includes computer-readable instructions that, when executed by processor 110, cause INS 26 to perform various functions. Memory 112 may include any volatile, non-volatile, magnetic, optical, or electrical media, such as a RAM, ROM, NVRAM, EEPROM, flash memory, or any other digital media. Electrical parameter values indicative of the interdevice impedance of patient 12 may be stored by memory 112, whereby the electrical parameter values may be determined using the techniques described herein. In addition, in some examples, a trend in the electrical parameter values over time may also be stored by memory 112. The trend may be indicated by, for example, a rate of change of the electrical parameter value over time.

Memory 112 may also store therapy programs, which may be stored in therapy program groups, and operating instructions. The therapy programs may define a particular program of therapy in terms of respective values for electrical stimulation parameters, such as electrode combination, electrode polarity, current or voltage amplitude, pulse width and pulse rate. A program group may comprise a plurality of therapy programs that may be delivered together on an overlapping or non-overlapping basis. The stored operating instructions may guide the general operation of INS 26 under control of processor 110, and may include instructions for determining impedance or communicating with ICD 16 via electrodes 124.

Signal generator 114 may generate stimulation signals, which may be pulses as primarily described herein, or continuous time signals, such as sine waves, for delivery to patient 12 via selected combinations of electrodes 124. In addition, signal generator 114 may also generate an electrical signal between two or more electrodes 124 in order to determine an electrical parameter value indicative of impedance of an electrical path between ICD 16 and INS 26 or to generate signals for communicating with INS 26.

Processor 110 controls signal generator 114 according to stored therapy programs and/or program groups in memory 112 to apply particular stimulation parameter values specified by one or more of programs, such as amplitude, pulse width, and pulse rate. Processor 110 may include any one or more microprocessors, controllers, a DSPs, ASICs, FPGAs, or equivalent discrete or integrated digital or analog logic circuitry, and the functions attributed to processor 110 herein may be embodied as software, firmware, hardware or any combination thereof.

Signal generator 114 and sensing module 115 are coupled to switching module 116. Processor 110 may control switching module 116 to apply the stimulation signals generated by signal generator 114 to selected combinations of electrodes 124. In particular, switching module 116 couples stimulation signals to selected conductors within leads 28 which, in turn, deliver the stimulation signals across selected electrodes 124. In addition, in some examples, processor 110 may control switching module 116 to connect a selected combination of electrodes 124 to sensing module 115 to sense electrical signals. The electrical signals may be, for example, a far field signal generated between electrodes 50, 52, 54, 56, 58, 60, 68, 72, 74, and 76 of leads 18, 20, 22 that are coupled to ICD 16. Switching module 116 may be a switch array, switch matrix, multiplexer, or any other type of switching device suitable to selectively couple stimulation energy to selected electrodes. Hence, signal generator 114 is coupled to electrodes 124 via switching module 116 and conductors within leads 28. In some examples, INS 26 does not include switching module 116.

Signal generator 114 may be a single- or multi-channel signal generator. In particular, signal generator 114 may be capable of delivering, a single stimulation pulse, multiple stimulation pulses, or a continuous signal at a given time via a single electrode combination or multiple stimulation pulses at a given time via multiple electrode combinations. In some examples, however, signal generator 114 and switching module 116 may be configured to deliver multiple channels on a time-interleaved basis. In this case, switching module 116 serves to time division multiplex the output of signal generator 114 across different electrode combinations at different times to deliver multiple programs or channels of stimulation energy to patient 12.

Sensing module 115 is configured to collect, determine and/or calculate impedance data for any of a variety of electrical paths that include two or more of electrodes 124. Processor 90 may additionally or alternatively collect, determine and/or calculate impedance data for any of a variety of electrical paths that include two or more of electrodes 124. In addition, in some examples, sensing module 115 is configured to collect, determine, and/or calculate impedance data for an impedance path between two or more electrodes 124 and two or more electrodes 50, 52, 54, 56, 58, 60, 68, 72, 74, and 76 of leads 18, 20, 22 that are coupled to ICD 16, as described in further detail below with reference to FIG. 9. For example, sensing module 96 may sense an electrical signal that is generated between two electrodes 50, 52, 54, 56, 58, 60, 68, 72, 74, and 76 of leads 18, 20, 22 that are coupled to ICD 16, and determine an impedance value or other electrical parameter value that indicates the impedance of the electrical path through tissue between ICD 16 and INS 26.

As another example, sensing module 115 may sense an electrical signal via two or more electrodes 124 and demodulate the signal, e.g., with the aid of processor 110, to extract information from the signal. Sensing module 115 may sense the intradevice signal generated by ICD 16 via a wide band channel, transmit the sensed signal through an analog-to-digital converter, and then digitally process the signal, e.g., with the aid of processor 110, to determine an transthoracic impedance, a value indicative of transthoracic impedance or to extract information communicated to INS 26 via the sensed signal. In some examples, sensing module 115 may also be configured to monitor signals from at least one of electrodes 124 in order to monitor physiological parameters of patient 12, such as EGM/ECG signals of heart 14 (FIG. 1).

Telemetry module 118 supports wireless communication between INS 26 and an external programmer 24 (FIG. 1) or another computing device under the control of processor 110. Processor 110 of INS 26 may receive, as updates to programs, values for various stimulation parameters such as amplitude and electrode combination, from programmer 24 via telemetry module 118. The updates to the therapy programs may be stored within memory 112.

The various components of INS 26 are coupled to power supply 120, which may include a rechargeable or non-rechargeable battery. A non-rechargeable battery may be selected to last for several years, while a rechargeable battery may be inductively charged from an external device, e.g., on a daily or weekly basis. In other examples, power supply 120 may be powered by proximal inductive interaction with an external power supply carried by patient 12.

Figure 8:
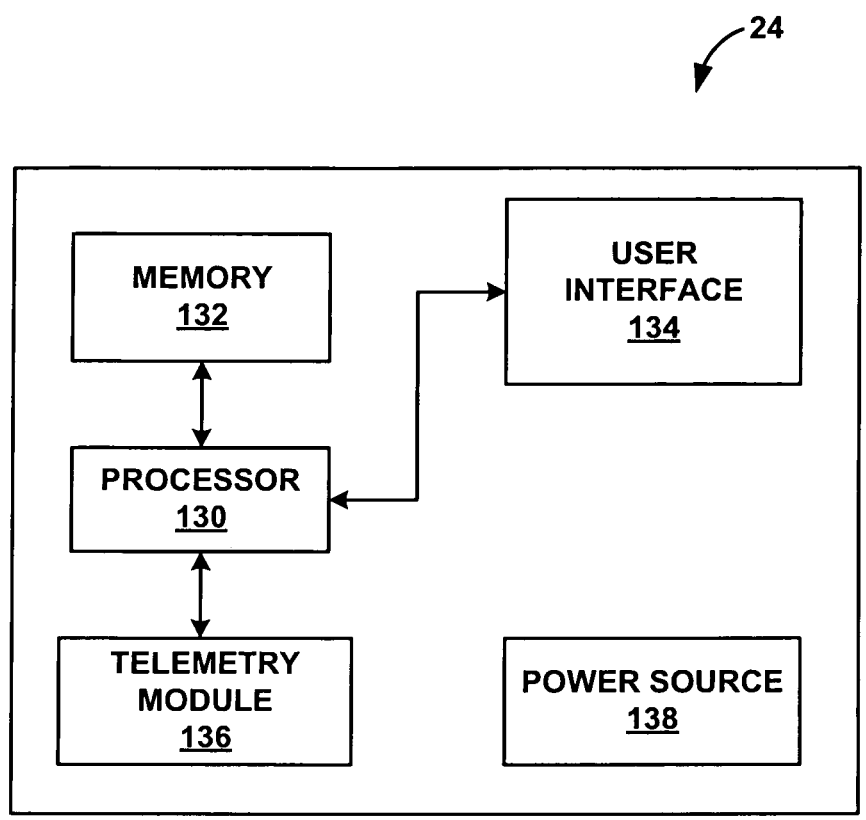
FIG. 8 is a functional block diagram of an example medical device programmer.

FIG. 8 is block diagram of an example programmer 24. As shown in FIG. 8, programmer 24 includes processor 130, memory 132, user interface 134, telemetry module 136, and power source 138. Programmer 24 may be a dedicated hardware device with dedicated software for programming of ICD 16 and INS 26. Alternatively, programmer 24 may be an off-the-shelf computing device running an application that enables programmer 24 to program ICD 16 and INS 26. In some examples, separate programmers may be used to program ICD 16 and INS 26. However, a common programmer 24 that is configured to program both ICD 16 and INS 26 may provide a more streamlined programming process for a user, such as a clinician or patient 12.

A user may use programmer 24 to select therapy programs (e.g., sets of stimulation parameters), generate new therapy programs, modify therapy programs through individual or global adjustments or transmit the new programs to a medical device, such as ICD 16 or INS 26 (FIG. 1). The clinician may interact with programmer 24 via user interface 134, which may include display to present graphical user interface to a user, and a keypad or another mechanism for receiving input from a user.

Processor 130 can take the form one or more microprocessors, DSPs, ASICs, FPGAs, programmable logic circuitry, or the like, and the functions attributed to processor 102 herein may be embodied as hardware, firmware, software or any combination thereof. Memory 132 may store instructions that cause processor 130 to provide the functionality ascribed to programmer 24 herein, and information used by processor 130 to provide the functionality ascribed to programmer 24 herein. Memory 132 may include any fixed or removable magnetic, optical, or electrical media, such as RAM, ROM, CD-ROM, hard or floppy magnetic disks, EEPROM, or the like. Memory 132 may also include a removable memory portion that may be used to provide memory updates or increases in memory capacities. A removable memory may also allow patient data to be easily transferred to another computing device, or to be removed before programmer 24 is used to program therapy for another patient. Memory 132 may also store information that controls therapy delivery by ICD 16 and INS 26, such as stimulation parameter values.

Programmer 24 may communicate wirelessly with ICD 16 and INS 24, such as using RF communication or proximal inductive interaction. This wireless communication is possible through the use of telemetry module 136, which may be coupled to an internal antenna or an external antenna. An external antenna that is coupled to programmer 24 may correspond to the programming head that may be placed over ICD 16 or INS 26, as described above with reference to FIG. 1. Telemetry module 136 may be similar to telemetry module 98 of ICD 16 (FIG. 6) or telemetry module 118 of INS 26 (FIG. 7).

Telemetry module 136 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 138 delivers operating power to the components of programmer 24. Power source 138 may include a battery and a power generation circuit to produce the operating power. In some examples, the battery may be rechargeable to allow extended operation. Recharging may be accomplished by electrically coupling power source 138 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 138 may include circuitry to monitor power remaining within a battery. In this manner, user interface 134 may provide a current battery level indicator or low battery level indicator when the battery needs to be replaced or recharged. In some cases, power source 138 may be capable of estimating the remaining time of operation using the current battery.

Figure 9:
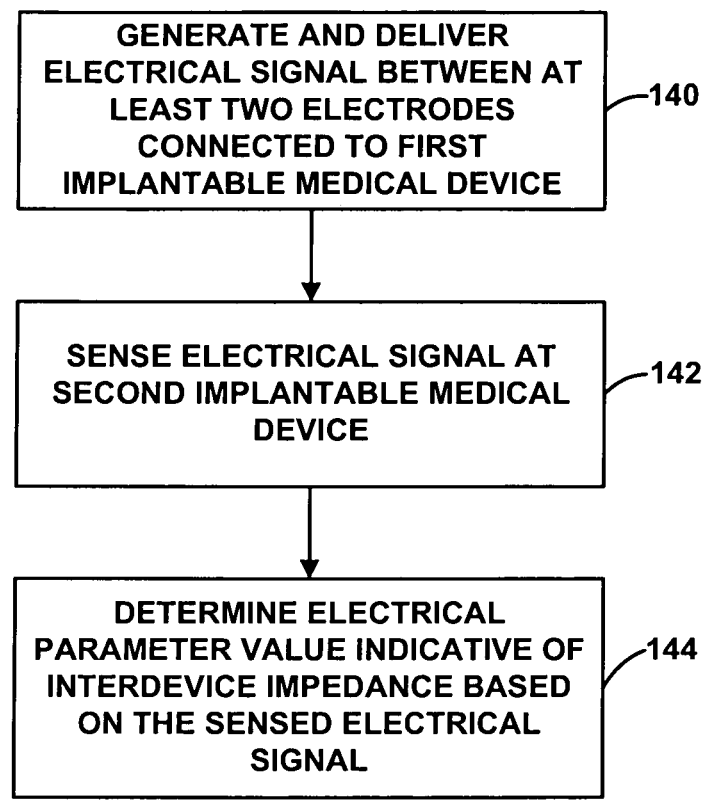
FIG. 9 is a flow diagram of an example technique for determining an impedance of an electrical path through tissue of a patient between an implanted ICD and an implanted INS.

FIG. 9 is a flow diagram of an example technique for determining an electrical parameter value indicative of an impedance of an electrical path through tissue of patient 12 between ICD 16 and INS 26. A first IMD of therapy system 10 may generate and deliver an electrical signal between at least two electrodes (140). The electrical signal may comprise single pulse or multiple pulses at a relatively high frequency (e.g., greater than 25 Hz or greater than 50 Hz), which could be used to generate a relatively continuous signal that represents respiration rate or blood flow changes over time. In some examples, the electrical signal does not provide stimulation therapy to patient 12 and patient 12 does not perceive the electrical signal, due to, for example, the amplitudes of such signals and/or the timing of delivery of such signals. For example, the electrical signals may comprise sub-threshold amplitude signals that may not stimulate heart 14 or capture or otherwise activate tissue (e.g., neurons, myocardial tissue, and/or muscle) of patient 12. In examples in which ICD 16 delivers the electrical signals between at least two electrodes 50, 52, 54, 56, 58, 60, 68, 72, 74, and 76, the signals may be delivered during a refractory period, in which case they also may not stimulate heart 14.

In some examples, ICD 16 may generate and transmit an electrical signal between at least two electrodes 50, 52, 54, 56, 58, 60, 68, 72, 74, and 76 (FIG. 3). Processor 90 of ICD 16 (FIG. 6) may control the delivery, from signal generator 94 (FIG. 6), of an electrical signal comprising a constant current (e.g., a voltage pulse) or a constant voltage (e.g., a current pulse) between first and second electrodes. In other examples, INS 26 may generate and transmit an electrical signal between at least two electrodes 124 (140). Processor 110 of INS 26 (FIG. 7) may control the delivery, from signal generator 114, of an electrical signal comprising a constant current or a constant voltage between two or more electrodes 124.

The delivery of the electrical signal by the first IMD may generate an electrical field in the body of patient 12, which may then be sensed by the second IMD of therapy system 10 (142). The second IMD is different than the first IMD and mechanically decoupled (e.g., independently movable) from the first IMD. For example, if ICD 16 is the first IMD that generates and transmits the electrical signal between at least two electrodes 50, 52, 54, 56, 58, 60, 68, 72, 74, and 76, INS 26 may be the second IMD that senses the far field signal generated by the transmission of the electrical signal between the electrodes. On the other hand, if INS 26 is the first IMD that generates and transmits the electrical signal between at least two electrodes 124, ICD 16 may be the second IMD that senses the far field signal generated by that transmission of the electrical signal between the electrodes by INS 26. Processor 90 of ICD 16 or processor 110 of INS 26 may determine the interdevice impedance based on one or more electrical parameter values of the sensed electrical signal (144).

In certain cases, the second IMD of therapy system may collect impedance values that include both a resistive and a reactive (i.e., phase) component. In such cases, the second IMD may determine impedance during delivery of a sinusoidal or other time varying signal by the signal generator of the first IMD. Thus, as used herein, the term "impedance" is used in a broad sense to indicate any collected, determined, and/or calculated value that may include one or both of resistive and reactive components. Moreover, in some cases, the second IMD may determine an electrical parameter value indicative of the impedance. For example, the second IMD may determine a current or voltage amplitude of the sensed signal, which may indicate the impedance of the electrical path between the first and second IMDs.

In examples in which ICD 16 generates and delivers an electrical signal comprising a constant voltage between at least two electrodes 50, 52, 54, 56, 58, 60, 68, 72, 74, and 76, sensing module 115 of INS 26 (FIG. 7) may determine a resulting current of the signal that is sensed by one or more electrodes 124. This resulting current may be an electrical parameter value indicative of the impedance of the electrical path between the first and second IMDs. In some examples, processor 110 of INS 26 or processor 90 of ICD 16 may determine a resistance based upon the voltage amplitude of the electrical signal generated by ICD 16 and the determined current amplitude of the signal sensed by INS 26. For example, if processor 110 of INS 26 determines the resistance, processor 90 of ICD 16 may communicate the voltage amplitude of the generated signal to INS 26 such that processor 110 has the information necessary to determine the resistance. The communication may be performed via the respective telemetry modules 98, 118 of ICD 16 and INS 26 or via the intradevice signals generated between the electrodes coupled to the respective device 16, 26. In other examples, the voltage amplitude of the transmitted electrical signal could also be assumed or know by the other device.

Processor 90 of ICD 16 may communicate the voltage amplitude of the generated signal to INS 26, e.g., by controlling signal generator 94 (FIG. 6) to generate an electrical communication signal between two or more electrodes 50, 52, 54, 56, 58, 60, 68, 72, 74, and 76. The electrical communication signal may or may not have therapeutic benefits. Processor 90 may encode information in the electrical communication signal. For example, the pattern of the pulses (e.g., three pulses at a frequency of about 50 Hz) of the communication signal may be associated with information and INS 26 may demodulate the sensed signal to detect the pattern and reference memory 102 (FIG. 7) to determine the information associated with the pattern. In other examples, processor 90 of ICD 16 may communicate the voltage amplitude of the generated signal to INS 26 via the respective telemetry modules 98 (FIG. 6), 118 (FIG. 7). ICD 16 may also transmit a communication signal to INS 26 using similar techniques to indicate the prospective delivery of the electrical signal for determining interdevice impedance. Upon receiving the communication signal, INS 26 may sense the electrical signal. In this way, ICD 16 and INS 26 may synchronize the interdevice impedance determination activities.

If processor 90 of ICD 16 determines the resistance, processor 110 of INS 26 may communicate the current amplitude of the sensed signal to ICD 16, such that processor 90 has the appropriate information to determine the resistance. The communication may be performed via the respective telemetry modules 98, 118 of ICD 16 and INS 26 or via the intradevice signals generated between the electrodes coupled to the respective device 16, 26. Just as with processor 90 of ICD 16, processor 110 of INS 26 may communicate the current amplitude of the sensed signal to ICD 16 by generating and delivering an intradevice signal, e.g., by controlling signal generator 114 (FIG. 7) to generate an electrical communication signal between two or more electrodes 124, and ICD 16 may sense the communication signal. Processor 110 may use similar encoding techniques to those described above with respect to processor 90.

The resistance-determining device 16 or 26 may transmit the determined resistance to the other device 26 or 16. In addition, the current or voltage amplitude could also be assumed or know by the other device.

In examples in which ICD 16 generates and delivers an electrical signal comprising a constant current between at least two electrodes 50, 52, 54, 56, 58, 60, 68, 72, 74, and 76, sensing module 115 of INS 26 may determine a resulting voltage of the sensed signal. The voltage of the sensed signal may be an electrical parameter value indicative of the impedance of the electrical path between the first and second IMDs. In other examples, the resistance of the electrical path may be the electrical parameter value indicative of the impedance of the electrical path between the first and second IMDs. For example, processor 110 of INS 26 or processor 90 of ICD 16 may determine a resistance based upon the current amplitude of the electrical signal generated by ICD 16 and the voltage amplitude of the signal sensed by INS 26.

Sensing module 115 of INS 26, as well as sensing module 96 of ICD 16, may include circuitry for determining amplitudes of resulting currents or voltages, such as sample and hold circuitry. In other examples, processor 110 of INS 26 may transmit the determined voltage of the sensed signal to processor 90 of ICD 16 via the respective telemetry modules 118, 98. Processor 90 of ICD 16 may determine the resistance of the electrical path between ICD 16 and INS 26 based on the current amplitude of the electrical signal generated and delivered by ICD 16 and the voltage amplitude of the signal sensed by INS 26. In addition, the current or voltage amplitude could also be assumed or know by the other device.

In examples in which INS 26 generates and delivers an electrical signal comprising a constant current between at least two electrodes 124, sensing module 96 of ICD 16 (FIG. 6) may determine a resulting current of the signal that is sensed by one or more electrodes 50, 52, 54, 56, 58, 60, 68, 72, 74, and 76 coupled to ICD 16. Processor 90 of ICD 16 may determine a resistance based upon the voltage amplitude of the electrical signal generated by INS 26 and the current amplitude of the signal sensed by ICD 16. In other examples, processor 90 of ICD 16 may transmit the current amplitude of the sensed signal to processor 110 of INS 26 via the respective telemetry modules 98, 118. In examples in which INS 26 generates and delivers an electrical signal comprising a constant voltage between least two electrodes 124, sensing module 96 of ICD 16 may determine a resulting voltage of the sensed signal. Processor 90 of ICD 16 or processor 110 of INS 26 may determine a resistance of the electrical path between ICD 16 and INS 26 based upon the current amplitude of the electrical signal generated by INS 26 and the voltage amplitude of signal sensed by ICD 16.

In some examples, processor 90 of ICD 16, processor 110 of INS 26 or a processor of another device (e.g., programmer) may store the determined electrical parameter value indicative of the impedance between ICD 16 and INS 26 in memory 92 of ICD 16 (FIG. 6), memory 112 of INS 26 (FIG. 7), memory 132 of programmer 24 (FIG. 8) or a memory of another device (e.g., a remote device, such as a clinician database or computer). As described in further detail below, a trend in a plurality of determined electrical parameter values over time may also be stored in memory 92 of ICD 16 (FIG. 6), memory 112 of INS 26 (FIG. 7), memory 132 of programmer 24 (FIG. 8) or a memory of another device. In addition, in some examples, the voltage or current of the sensed electrical signal, and the voltage or current amplitude of the transmitted electrical signal may be stored the memory. In some examples, the voltage or current of the sensed electrical signal, and the voltage or current amplitude of the transmitted electrical signal may be transmitted to another device (e.g., a remote computing device) and the device may determine the impedance value. This may be more efficient than determining the impedance value via a processor of ICD 16 or INS 26.

Figure 10:
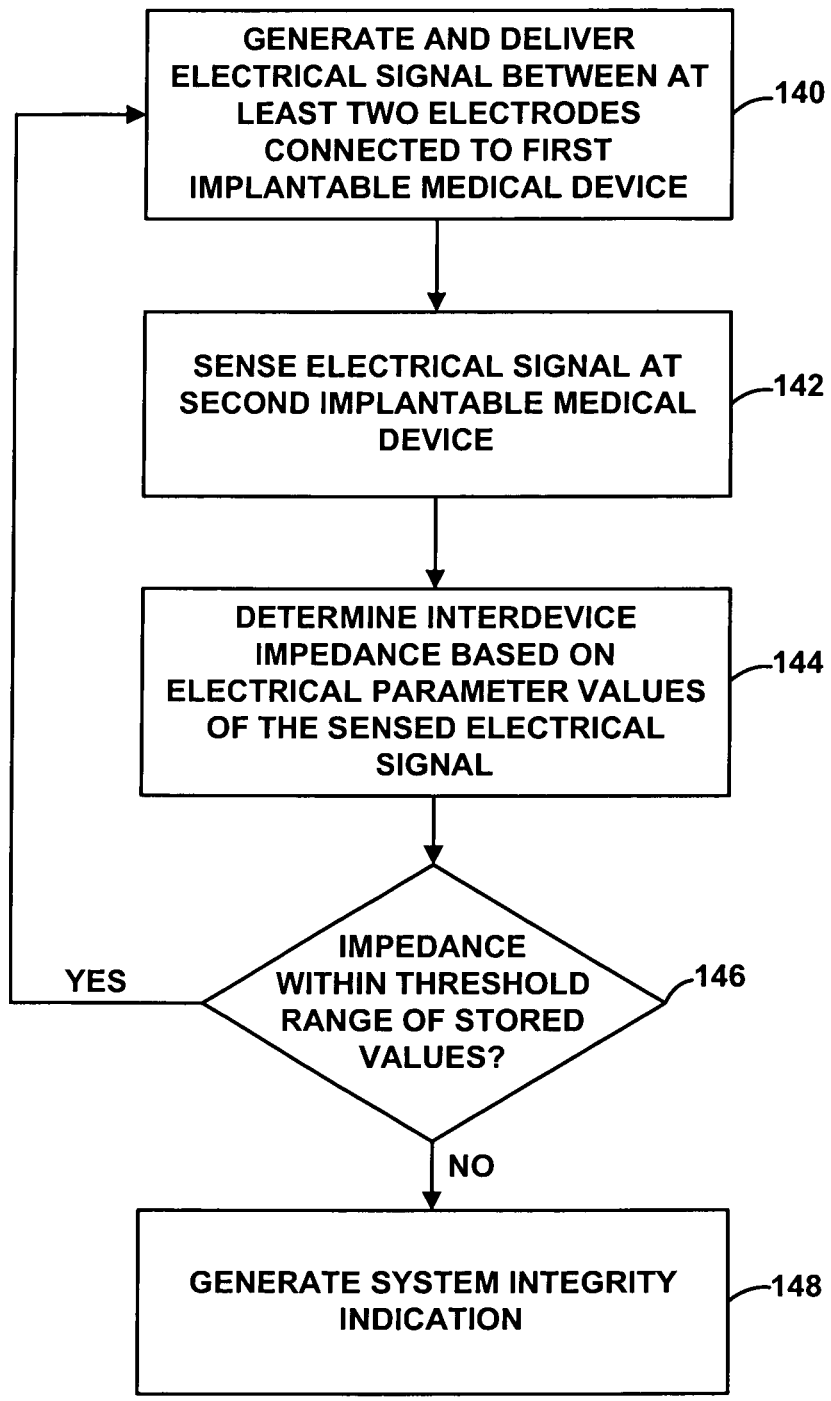
FIG. 10 is a flow diagram of an example technique for determining whether an impedance of an electrical path through tissue of a patient between an implanted ICD and an implanted INS indicates a system integrity issue.

FIG. 10 is a flow diagram of an example technique that may be implemented in order to determine whether the interdevice impedance indicates a system integrity issue is present. A system integrity issue may indicate, for example, that one of leads 18, 20, 22, 28 of therapy system 10 have moved or that the housings of ICD 16 and INS 26 have moved. For example, processor 90 of ICD 16, processor 110 of INS 26 or a processor of another device (e.g., programmer 24) may determine whether the electrodes of one or more of leads 18, 20, 22, housing 70 of ICD 16 have moved relative to the electrodes of one or more of leads 28, 29 or housing 122 of INS 26.

As with FIG. 9, a first IMD (e.g., ICD 16 or INS 26) may generate and deliver an electrical signal between at least two electrodes that are electrically coupled to the first IMD (140). A second IMD (e.g., INS 26 or ICD 16) may sense the electrical signal that is delivered between the electrodes coupled to the first IMD (142). Processor 90 of ICD 16 or processor 110 of INS 26 may determine an electrical parameter value indicative of the interdevice impedance based on the electrical signal sensed by the second IMD (144). In some examples, the electrical parameter value indicative of the interdevice impedance may be a mean or median electrical parameter value that is determined based on a plurality of interdevice impedance determinations. For example, the electrical parameter value indicative of the interdevice impedance may be a mean or median electrical parameter value of a plurality of interdevice impedance determinations made over the course of a seconds (e.g., 30 seconds), minutes, hours or even days.

Processor 90 of ICD 16 or processor 110 of INS 26 may compare the determined interdevice impedance value to a stored impedance value (146). In the technique shown in FIG. 10, processor 90 of ICD 16 or processor 110 of INS 26 may determine whether the determined interdevice impedance value is within a predetermined range of impedance values, e.g., within a range of a stored impedance value (146). Both the stored impedance value and the threshold range may be stored within memory 92 of ICD 16 (FIG. 6), memory 112 of INS 26 (FIG. 7), memory 132 of programmer 24 (FIG. 8) or a memory of another device. The stored impedance value may be an electrical parameter value indicative of the impedance of the electrical path between ICD 16 and INS 26 when leads 18, 20, 22, 28 and housings of ICD 16 and INS 26 are in a known location relative to each other. For example, shortly after implanting therapy system 10 within patient 12, a clinician may determine the interdevice impedance between ICD 16 and INS 26 using any suitable combination of electrodes and store the determined interdevice impedance in memory 92 of ICD 16 (FIG. 6), memory 112 of INS 26 (FIG. 7), memory 132 of programmer 24 (FIG. 8) or a memory of another device.

The threshold range may be a range of acceptable interdevice impedance values. For example, the threshold range may indicate the amount with which the determined interdevice impedance may vary without adversely affecting the efficacy of therapy delivery by either or both ICD 16 and INS 26. As an example, a determined interdevice impedance within the threshold range of a stored value may indicate ICD 16, INS 26, and the respective leads 18, 20, 22, 28 have not moved or have moved within an acceptable distance range. As another example, the threshold range may indicate a range of values within which an interdevice impedance may fluctuate due to changes in the physiological make-up of patient (e.g., a hydration level of patient 12). The threshold range may be specific to patient 12 or may be applicable to more than one patient 12 (e.g., may be general to a particular class of patients). The threshold range may be programmed, e.g., via programmer 24 (FIG. 1).

In other examples, rather than storing an impedance value and a threshold range, first and second impedance values may be stored within memory 92 of ICD 16 (FIG. 6), memory 112 of INS 26 (FIG. 7), memory 132 of programmer 24 (FIG. 8)

or a memory of another device. The interdevice impedance values that are greater than the first stored impedance value, but less than the second stored impedance value may indicate the acceptable range of values.

In some examples, the threshold range of impedance values may be dynamic, and may change based on the time of day, the patient's posture, the patient's hydration level, and the like. For example, one or more memories 92, 112, 132 may store a plurality of threshold ranges and associate the ranges with an accelerometer output that is indicative of patient posture or patient activity level. ICD 16, INS 26 or another device may include an accelerometer (e.g., a multi-axis accelerometer, such as a three-axis accelerometer), and processor 90 of ICD 16, processor 110 of INS 26 or another device may select the appropriate threshold range based on the output from the accelerometer. If the accelerometer is separate from ICD 16 or INS 26, the accelerometer may transmit an electrical signal indicative of patient posture to the appropriate device 16, 26 via wireless communication techniques or via a wired communication line. In some examples, the accelerometer may be external to patient 12 (e.g., worn on a wristband).

As another example of a dynamic threshold, the stored range of impedance values may be based on the mean or median interdevice impedance values for a period of time preceding the current interdevice impedance determination. Thus, if the current interdevice impedance determination (144) differs from the mean or median interdevice impedance value by a certain amount (e.g., an absolute value or a percentage-based value), the current interdevice impedance determination may not be within the stored range of values (146).

In other examples, the threshold range of impedance values that indicate an acceptable system integrity condition or an acceptable patient physiological condition may be based on the rate of change of the impedance values. As described with respect to FIG. 11, ICD 16, INS 26 or another device may track the interdevice impedance values over time. If a relatively fast rate of change is detected, e.g., within a predetermined time span, processor 90 of ICD 16, processor 110 of INS 26 or another device may select a threshold range from a plurality of stored threshold ranges based on the temporal activity of the interdevice impedance values. For example, if the rate of change is relatively fast (e.g., exceeds a predetermined threshold) because patient 12 is relatively active and, therefore, the fluid status of patient 12 is changing relatively fast, a larger range of impedance values may be selected. In this way, ICD 16 or INS 26 may be less sensitive to the relatively large fluctuations in the interdevice impedance values that may be due to factors other than the patient's health and system integrity issues.

Different threshold impedance values may be stored, and may be associated with the different electrical paths between ICD 16 and INS 26. For example, an impedance value that results when a voltage pulse is delivered between electrode 52 of lead 18 and housing electrode 68 and is sensed by electrode 124A coupled to INS 26 may be different than an impedance value that results when a voltage pulse is delivered between electrode 52 of lead 18 and housing electrode 68 and is sensed by electrode 124B. In addition, an impedance value that results when a voltage pulse is delivered between electrode 52 of lead 18 and housing electrode 68 and is sensed by electrode 124A may be different than an impedance value that results when a voltage pulse is delivered between electrode 50 of lead 18 and electrode 54 of lead 20 and is sensed by electrode 124A. Thus, different threshold impedance values may be stored for the different combinations of electrodes that may be selected to determine interdevice impedance. In examples in which a different electrical parameter value indicative of the interdevice impedance is used, different threshold values may be stored for the electrical parameter value for the different combinations of electrodes that may be selected to determine interdevice impedance.

If processor 90 of ICD 16 compares the determined interdevice impedance value with the stored impedance value and determines that the determined interdevice impedance value is within the threshold range of stored values, processor 90 may continue controlling signal generator 94 to generate and deliver electrical signals in order to determine an interdevice impedance again. If processor 110 of INS 26 compares the determined interdevice impedance value with the stored impedance value and determines that the determined interdevice impedance value is within the threshold range of stored values, processor 110 may not take any action.

If the determined interdevice impedance value is within the threshold range of stored values, one or both processors 90, 110 may determine that the patient's fluid status, as indicated by an intrathoracic impedance, is within acceptable limits. In addition, one or both processors 90, 110 may determine that the system integrity is not an issue. For example, one or both processors 90, 110 may determine that the interdevice impedance values indicate that one or more electrodes leads 18, 20, 22 or housing 70 of ICD 16 have not shifted relative to one or more electrodes of leads 28, 29 or housing 122 of INS 26.

In some cases, processor 110 may notify processor 90 that the determined interdevice impedance was within the threshold range of the stored impedance value. Processor 110 of INS 26 and processor 90 of ICD 16 may communicate using any suitable technique. For example, processor 110 and processor 90 may communicate via the respective telemetry modules 98, 118. As another example, processor 110 may communicate with processor 90 by controlling signal generator 114 (FIG. 7) to transmit an electrical signal having a signal characteristic that is less than the activation threshold of patient 12 between two or more electrodes 124 of lead 28. ICD 16 may then sense the signal via sense electrodes coupled to leads 18, 20, 22 or housing 70 and demodulate the signal to extract the information from INS 26.

System 10 may determine the interdevice impedance at any particular sampling frequency, such as about one to four times per day, although other frequencies are contemplated. For example, processor 90 of ICD 16 may be configured to control signal generator 94 to generate and deliver electrical signals in order to determine an interdevice impedance at a predetermined sampling frequency (e.g., about one to four times per day). A higher sampling frequency (e.g., about once per hour, or about 0.5 Hertz (Hz) to about 100 Hz) may provide a better temporal resolution of the transthoracic impedance values over time, which may be useful for determining respiration rate or blood flow.

If processor 90 of ICD 16 or processor 110 of INS 26 determines that the determined interdevice impedance value is not within the threshold range of stored values, the respective processor 90, 110 may generate a system integrity indication (148). The system integrity indication may be a value, flag, or signal that is stored or transmitted to another device, such as programmer 24. The sensing integrity indication may be stored within ICD 16, INS 26 or programmer 24 along with the associated date stamp and any other relevant information for later retrieval and analysis by a clinician.

The sensing integrity indication may be used for later analysis of therapy system 10 by a clinician or to generate an alert to patient 12 that therapy system 10 may need to be checked by a clinician. In some examples, processor 90 of ICD 16, processor 110 of INS 26 or processor 130 of programmer 24 may recommend a corrective action upon alerting a clinician. For example, processor 90, 110, or 130 may recommend that one of the leads 18, 20, 22 be checked for a loose connection with connector block 48 (FIG. 3) of ICD 16, or that the position of one or more leads be verified by imaging, e.g., fluoroscopy.

The alert may be transmitted to the clinician or patient 12, e.g., via ICD 16, INS 26, programmer 24 or another implanted or external device, as described below with respect to FIG. 13. The alert generated by ICD 16, INS 26 or another implanted device may be, for example, an audible or somatosensory (e.g., vibration of a housing of ICD 16 or INS 26) notification to patient 12. Similarly, the alert generated by programmer 24 or another external device may include an audible or somatosensory notification, as well as a visible notification. A characteristic of the alert (or indication) to patient 12 or a clinician may change as a function of the severity of the detected sensing integrity issue. For example, the intensity of the audible sound, the pitch or frequency of the audible sound, the intensity somatosensory alert, the pattern of a vibration or other somatosensory sensation, the intensity of a visible alert or another characteristic of the audible, somatosensory or visible alert may change based on the detected interdevice impedance value and/or its relationship to the threshold range of stored values. In some cases, the detected sensing integrity issue may be indicated by the extent to which the interdevice impedance value falls outside of the threshold range.

Generation of the sensing integrity indication may also be used to control the therapy delivery by INS 26 or ICD 16. For example, upon generation of the sensing integrity indication that indicates leads 28, 29 electrically connected to INS 26 may have migrated, INS 26 may suspend therapy delivery. If ICD 16 detects the intrathoracic impedance value that indicates leads 28, 29 have moved and generates the sensing integrity indication, ICD 16 may transmit the sensing integrity indication to INS 26. Upon receiving the sensing integrity indication, INS 26 may suspend therapy delivery, e.g., until user intervention is received. As previously described, it may be undesirable for electrodes of leads 28, 29 to migrate towards heart 14 because the electrical stimulation delivered via the electrodes may capture heart 14 and pace heart 14. The pacing of heart 14 may be undesirable because if the frequency of the stimulation signal generated by INS 26 is high enough, the pacing of heart 14 via the stimulation signals may induce an arrhythmia.

In other examples, upon receiving the sensing integrity indication or generating the sensing integrity determination, either INS 26 or ICD 16 may modify one or more therapy parameter values. For example, INS 26 may modify one or more therapy parameter values (e.g., by switching therapy programs or by modifying a specific therapy parameter value) to deliver stimulation signals having a lower frequency in order to decrease the possibility of inducing an arrhythmia.

In some examples, therapy system 10 may perform the technique shown in FIG. 10 with multiple combinations of electrodes in order to determine the interdevice impedance at multiple vectors. For example, signal generator 94 (FIG. 6) of ICD 16 may generate an electrical signal between electrodes 50, 52 (FIG. 6) and sensing module 116 (FIG. 7) of INS 26 may sense the electrical signal via electrodes 124A, 124B (FIG. 7) to determine a first electrical parameter value indicative of the impedance between ICD 16 and INS 26, and, in this example, between electrodes 50, 52 and electrodes 124A, 124B. In addition, signal generator 94 (FIG. 6) of ICD 16 may generate an electrical signal between electrodes 54, 56 (FIG. 6) and sensing module 116 (FIG. 7) of INS 26 may sense the electrical signal via electrodes 124A, 124B (FIG. 7) to determine a second electrical parameter value indicative of the impedance between ICD 16 and INS 26, and, in this example, between electrodes 50, 52 and electrodes 124A, 124B.

Processor 90 of ICD 16, processor 110 of INS 26, or a processor of another device may determine whether lead 28 connected to INS 26 has moved relative to ICD 16 (e.g., housing 70 or leads connected thereto) based on the first and second electrical parameter values. For example, the processor may compare a ratio of the first and second electrical parameter values indicative of interdevice impedance to a threshold value (or threshold ranges) to determine whether the lead 28 has moved relative to ICD 16. As another example, the processor may compare the first and second electrical parameter values to different threshold values (or threshold ranges) and detect lead movement based on the comparisons.

In some examples, more than two electrical parameters may be used, where each electrical parameter value is based on electrical signals transmitted by the first IMD via different electrode combinations and/or sensed by the second IMD via different electrode combinations. In the example described above, the first IMD uses different electrode combinations to transmit multiple electrical signals and the second IMD uses the same electrode combination to sense each transmitted electrical signal. In other examples, the first IMD may use the same electrode combinations to transmit multiple electrical signals and the second IMD may use different electrode combinations to sense each transmitted electrical signal. In yet other examples, the first IMD may use different electrode combinations to transmit multiple electrical signals and the second IMD may use different electrode combinations to sense each transmitted electrical signal.

Using more than one electrical parameter value to detect lead movement may provide a more robust indication of the lead movement, e.g., in more than one dimension, because the different electrical parameter values may be indicative of different sensing vectors. This may provide a better indication of lead movement or the extent of lead movement by detecting lead movement from different relative directions between ICD 16 and INS 26. In this way, the movement of the leads 18, 20, and/or 22 relative to leads 28 and/or 29 may be spatially constructed based on the electrical parameter values indicative of the impedance of different electrical paths.

Figure 11:
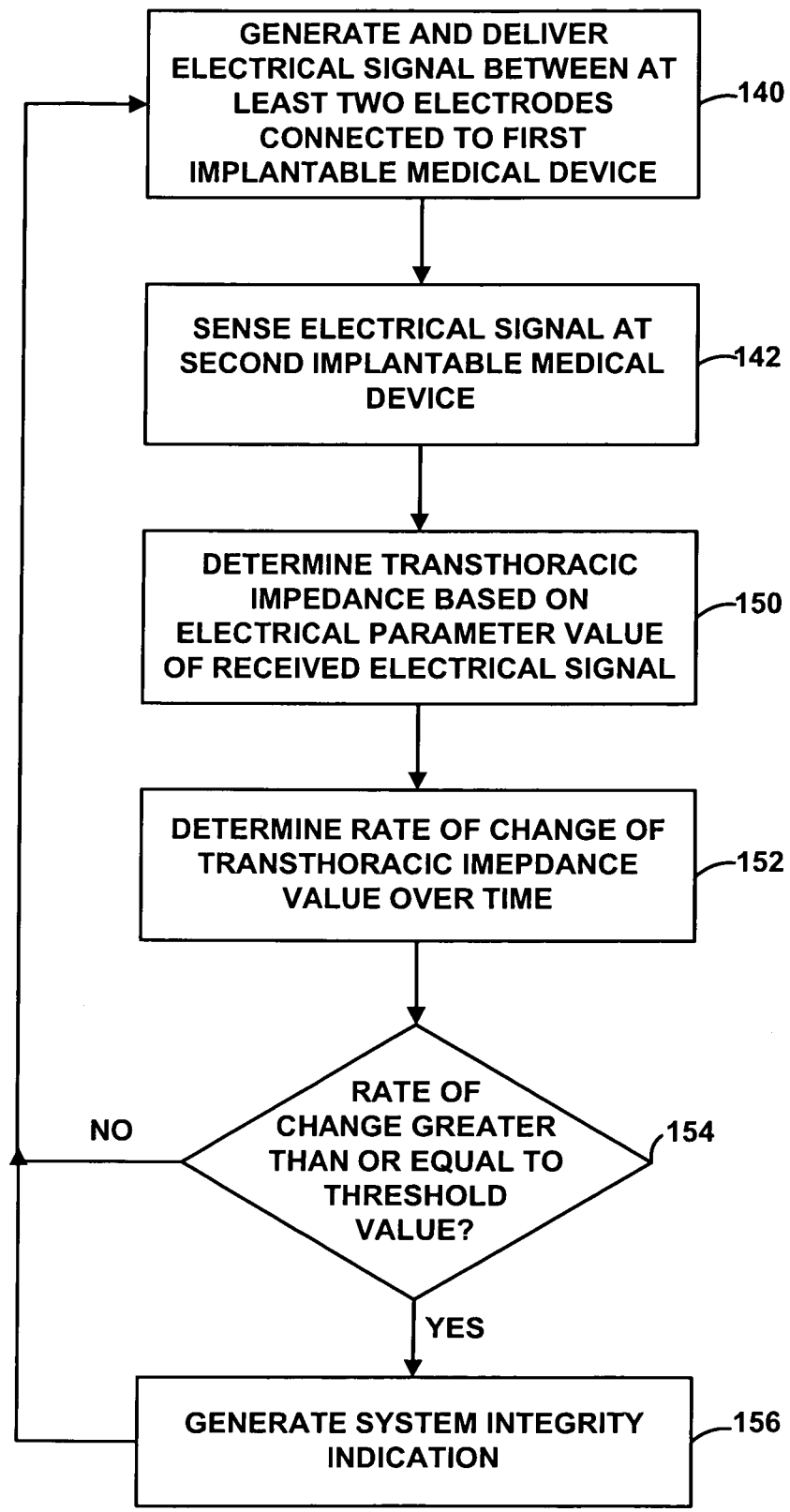
FIG. 11 is a flow diagram of an example technique for determining whether an impedance of an electrical path through tissue of a patient between an implanted ICD and an implanted INS is attributable to a factor such as patient posture or movement or a lead integrity issue.

FIG. 11 is a flow diagram illustrating an example technique for determining whether a change in an interdevice impedance indicates a lead-related condition. As previously indicated, a lead-related condition may include a fractured conductor of one or more leads 18, 20, 22, 28, a loose set-screw connecting one or more of the leads 18, 20, 22, 28 to the respective device 16, 26, or a change in the electrical insulation separating one or more conductors within a lead 18, 20, 22 or 28. A change in the electrical insulation may include, for example, wearing of the electrical insulation.

A first IMD of therapy system 10 may generate and deliver an electrical signal between at least two electrodes (140). The delivery of the electrical signal by the first IMD may generate an electrical field in the body of patient 12, which may then be sensed by the second IMD of therapy system 10 (142). Processor 90 of ICD 16 or processor 110 of INS 26 may determine a transthoracic impedance (or, more generally, interdevice impedance) based on at least one electrical parameter value of the electrical signal sensed by the second IMD (150).

Processor 90 of ICD 16 or processor 110 of INS 26 may determine a rate of change of the determined transthoracic impedance over time (152). For example, processor 90 or 110 may periodically determine an electrical parameter value indicative of the impedance between ICD 16 and INS 26 and store the determined electrical parameter values, e.g., in memory 92, 112, respectively. Processor 90 or 110 may then track the impedance values over time and determine, for example, a rate of change using known techniques. For example, processor 90 or 110 may determine the difference between a first electrical parameter value and a second electrical parameter value and divide the difference by the interval of time separating the time in which the first and second electrical parameter values were determined.

Processor 90 may compare the rate of change to a threshold value (154). The threshold value may be stored in memory 92 of ICD 16, memory 112 of INS 26 or a memory of another device (e.g., programmer 24). The threshold value may indicate a rate of change of an impedance value that is attributable to normal physiological changes in the patient's fluid status, e.g., due to changes in the patient's health. Physiologic changes that may affect intrathoracic impedance may take place over a known time course, and, accordingly, the transthoracic impedance values may change at a relative slow rate compared to changes in interdevice impedance attributable to lead-related conditions. For example, changes in transthoracic impedance due to congestive heart failure may take place over the course of a few days. Accordingly, a rate of change of intrathoracic impedance values that exceed a threshold of change may be indicative of an issue other than the patient's health, such as a system integrity issue (e.g., a lead-related condition) or changes to the patient's posture or activity level. In this way, the rate of change of electrical parameter values indicative of intrathoracic impedance over time may be indicative of a cause of the change in the intrathoracic impedance.

Thus, if processor 90 determines that the rate of change in the interdevice impedance value is greater than or equal to a threshold value (154), processor 90 may generate a system integrity indication (156). The system integrity indication may be indicative of a lead-related condition. The lead-related condition may result in a change in determined impedance at a faster rate than changes in transthoracic impedance due to the patient's fluid status or other physiological conditions. The system integrity indication may be transmitted to programmer 24, which may generate an alert to notify patient 12, clinician, or another person that clinician attention is desirable because a system integrity issue was identified. The alert may be, for example, a visual alert, an audible alert or a somatosensory alert. In some examples, ICD 16 or INS 26 may generate the alert, e.g., by vibrating or providing another somatosensory indication. In other examples, programmer 24 or another external device may receive the system integrity indication from one of the implanted devices 16, 26 and generate the alert to notify patient 12, a caretaker or clinician that the system integrity issue was detected.

In some examples, ICD 16 or INS 26 may modify one or more therapy parameter values upon generation of the system integrity indication. If ICD 16 or INS 26 did not generate the indication, ICD 16 or INS 26 may receive the indication from the generating device, e.g., via the respective telemetry modules 98 (FIG. 6), 118 (FIG. 7). In some examples, ICD 16 or INS 26 may modify one or more therapy parameter values by suspending therapy delivery until the system integrity indication is reset, e.g., by a clinician. In other examples, ICD 16 or INS 26 may modify one or more therapy parameter values by changing the electrode combination with which ICD 16, INS 26, respectively, delivers therapy to patient 12 and/or senses physiological parameters (e.g., cardiac activity) of patient 12. In other examples, ICD 16 or INS 26 may modify one or more therapy parameter values by modifying one or more stimulation parameter values, such as the voltage or current amplitude of the stimulation signal delivered to patient 12, the frequency of the signal, and the like.

In some examples, in order to help minimize the possibility that the rate of change of the transthoracic impedance is at least partially attributable to the patient's posture or activity level, processor 90, 110 may reference a motion sensor or posture sensor (e.g., an accelerometer) to determine the patient's current posture or activity level. Memory 92 of ICD 16, memory 112 of INS 26 or a memory of another device (e.g., programmer) may store a plurality of the threshold values and associated with impedance values. Processor 90 or 110 may select the appropriate threshold value based on the detected posture or activity level. In this way, processor 90, 110 may adapt the threshold value indicative of an unacceptable rate of change of a transthoracic impedance to the patient's activity level. Other techniques for accounting for changes in the patient's transthoracic impedance due to changes in patient posture or activity level may also be employed.

Figure 12:
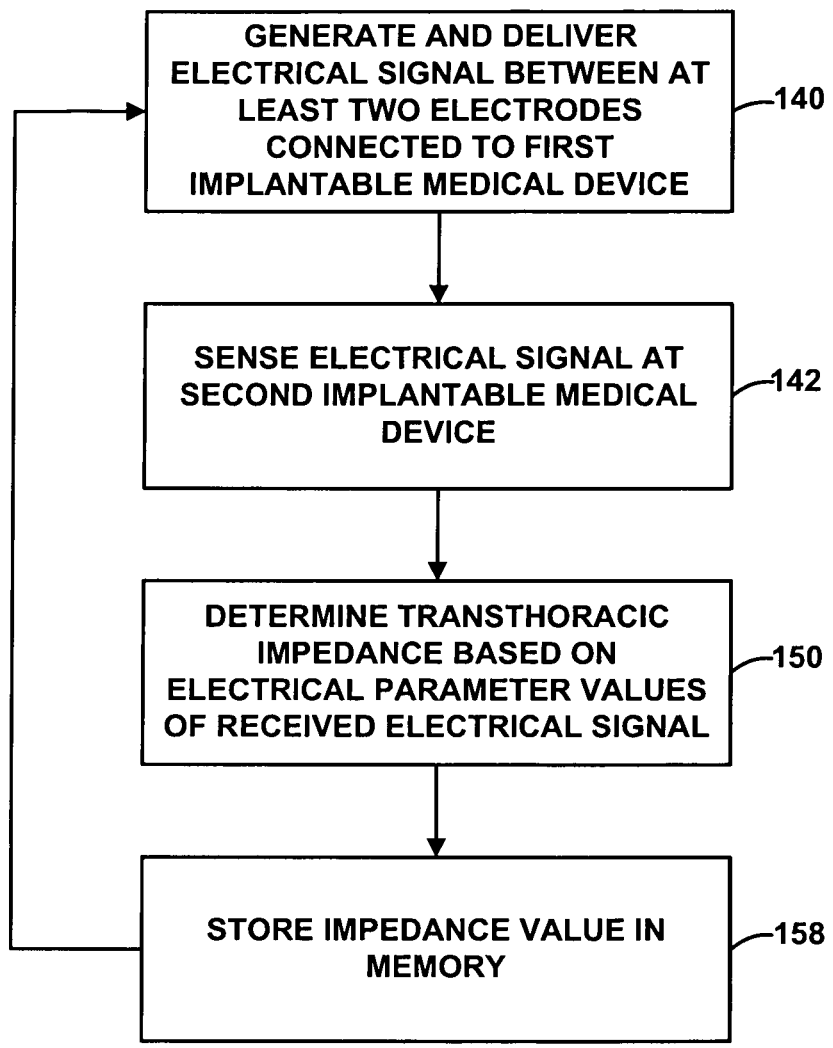
FIG. 12 is a flow diagram illustrating an example technique for determining a transthoracic impedance of a patient.

FIG. 12 is a flow diagram illustrating an example technique for determining a transthoracic impedance of patient 12. As with FIG. 9, a first IMD (e.g., ICD 16 or INS 26) may generate and deliver an electrical signal between at least a first electrode and a second electrode that are electrically coupled to the first IMD (140). The electrical signal that is transmitted between electrodes coupled to the first IMD may create an electrical field in the body of patient 12. This electrical field may be sensed by a second IMD (e.g., INS 26 or ICD 16) (142). The vector between ICD 16 and INS 26 may define a vector across the patient's thorax. Accordingly, processor 90 of ICD 16 or processor 110 of INS 26 may determine a transthoracic impedance based on at least one electrical parameter value of the electrical signal sensed by the second IMD (150).

As previously described, in some examples, ICD 16 may generate and deliver an electrical signal comprises a constant current or an electrical signal comprising a constant voltage between at least two electrodes 50, 52, 54, 56, 58, 60, 68, 72, 74, and 76 coupled to ICD 16. Sensing module 115 of INS 26 (FIG. 7) may determine a current or voltage of the signal (or electrical field) that is sensed by one or more electrodes 124. In examples in which ICD 16 generates an electrical signal comprising a constant current, processor 110 of INS 26 may determine a resistance of the electrical path between ICD 16 and INS 26 based upon the current or voltage amplitude of the electrical signal and the determined current amplitude of the electrical signal sensed by INS 26. The resistance indicates the transthoracic impedance. In other examples, processor 110 of INS 26 may transmit the determined current of the sensed signal to processor 90 of ICD 16 via the respective telemetry modules 118, 98. Processor 90 of ICD 16 may then determine the resistance based on the voltage amplitude of the electrical signal generated and delivered by ICD 16 and the current amplitude of the signal sensed by INS 26.

In examples in which ICD 16 generates an electrical signal comprising a constant voltage between at least two electrodes 50, 52, 54, 56, 58, 60, 68, 72, 74, and 76, sensing module 115 of INS 26 may determine a resulting voltage or current of the sensed signal. Processor 110 of INS 26 or processor 90 of ICD 16 may determine a resistance based upon the voltage or current amplitude of the electrical signal and the determined current or voltage amplitude, respectively, of the signal sensed by INS 26. Again, in other examples, processor 110 of INS 26 may transmit the determined voltage of the sensed signal to processor 90 of ICD 16 via the respective telemetry modules 118, 98. Processor 90 of ICD 16 may then determine the resistance of the path between ICD 16 and INS 26 based on the current amplitude of the electrical signal generated and delivered by ICD 16 and the voltage amplitude of the signal sensed by INS 26.

Alternatively, INS 26 may generate and deliver an electrical signal comprising a constant current or a constant voltage between at least two electrodes 124, sensing module 96 of ICD 16 (FIG. 6) may determine a current or voltage of the signal that is sensed by one or more electrodes 50, 52, 54, 56, 58, 60, 68, 72, 74, and 76 of leads 18, 20, 22 or housing 70. Processor 90 of ICD 16 or processor 110 of INS 26 may determine a resistance of the path between ICD 16 and INS 26 based on the current or voltage amplitude of the transmitted signal and the determined current or voltage amplitude of the signal sensed by ICD 16, where the resistance indicates the transthoracic impedance of patient 12.

After determining the transthoracic impedance based on the signal delivered by one device 16 or 26 and sensed by the other device 26 or 16, processor 90 of ICD 16 or processor 110 of INS 26 may store the determined transthoracic impedance value (158). The impedance value may be stored within memory 92 of ICD 16 (FIG. 4), memory 112 of INS 26 (FIG. 7), memory 132 of programmer 24 (FIG. 8) or a memory of another device, which may be, for example, a remote device (e.g., as described with respect to FIG. 13). In other examples, processor 90 of ICD 17 or processor 110 of INS 26 may not determine the transthoracic impedance values (150), but may instead store another electrical parameter value indicative of the transthoracic impedance value, such as a current or voltage amplitude of the signal sensed by the second IMD.

Therapy system 10 may continue determining the transthoracic impedance or otherwise determining an electrical parameter value indicative of the transthoracic impedance of patient 12 using the technique shown in FIG. 12 and storing the various electrical parameter values in memory (158). For example, therapy system 10 may determine the transthoracic impedance at a sampling frequency of such as about one to four times per day, although other frequencies are contemplated. The impedance values may be stored with an indication of a date and time that the impedance value was determined. A clinician may retrieve the stored transthoracic impedance values and, for example, evaluate the efficacy of therapy system 10 based on the impedance values, modify the therapy parameter values of ICD 16 and/or INS 26, and the like.

The electrical parameter value indicative of transthoracic impedance of patient 12 may be used to monitor the cardiac function of patient 12. For example, as previously indicated, an electrical parameter value indicative of transthoracic impedance may be used to determine how much fluid is present in the patient's thorax, which may be used to detect or predict congestive heart failure, pulmonary edema, pleural effusion, blood volume, hypertension, hypotension or other patient conditions. Decreases in transthoracic impedance may indicate increases in fluid content within the patient's thorax and increases in transthoracic impedance may indicate decreases in fluid content. In other examples, processor 90 (FIG. 6) of ICD 16, processor In some examples, the determined transthoracic impedance values may be used to control ICD 16 and/or INS 26 in a closed-loop therapy system. For example, as previously described, transthoracic impedance values may indicate the respiration rate of patient 12, and the respiration rate may be used to control the rate at which ICD 16 delivers pacing pulses to patient 12. In addition, as previously discussed, if a decrease in transthoracic impedance is detected, ICD 16 and INS 26 may increase the intensity of therapy (e.g., the frequency of stimulation signals or the voltage or current amplitude, pulse width, duty cycle, and the like) in order to help improve the patient's cardiac function.

In other examples, the determined transthoracic impedance values may be used to generate an indication (e.g., an alert) that notifies patient 12, a clinician, a caregiver or another person of the determined transthoracic impedance value. For example, if the determined transthoracic impedance value falls below a stored threshold value or exceeds a stored value, processor 90 of ICD 16 or processor 110 of INS 26 may generate an alert (e.g., a vibrating alert or an audible alert) or transmit an indication to programmer 24, which may generate a visual, auditory or a somatosensory (e.g., pulse vibrations) alert. Upon receiving the alert, patient 12 may seek medical attention.

Figure 13:
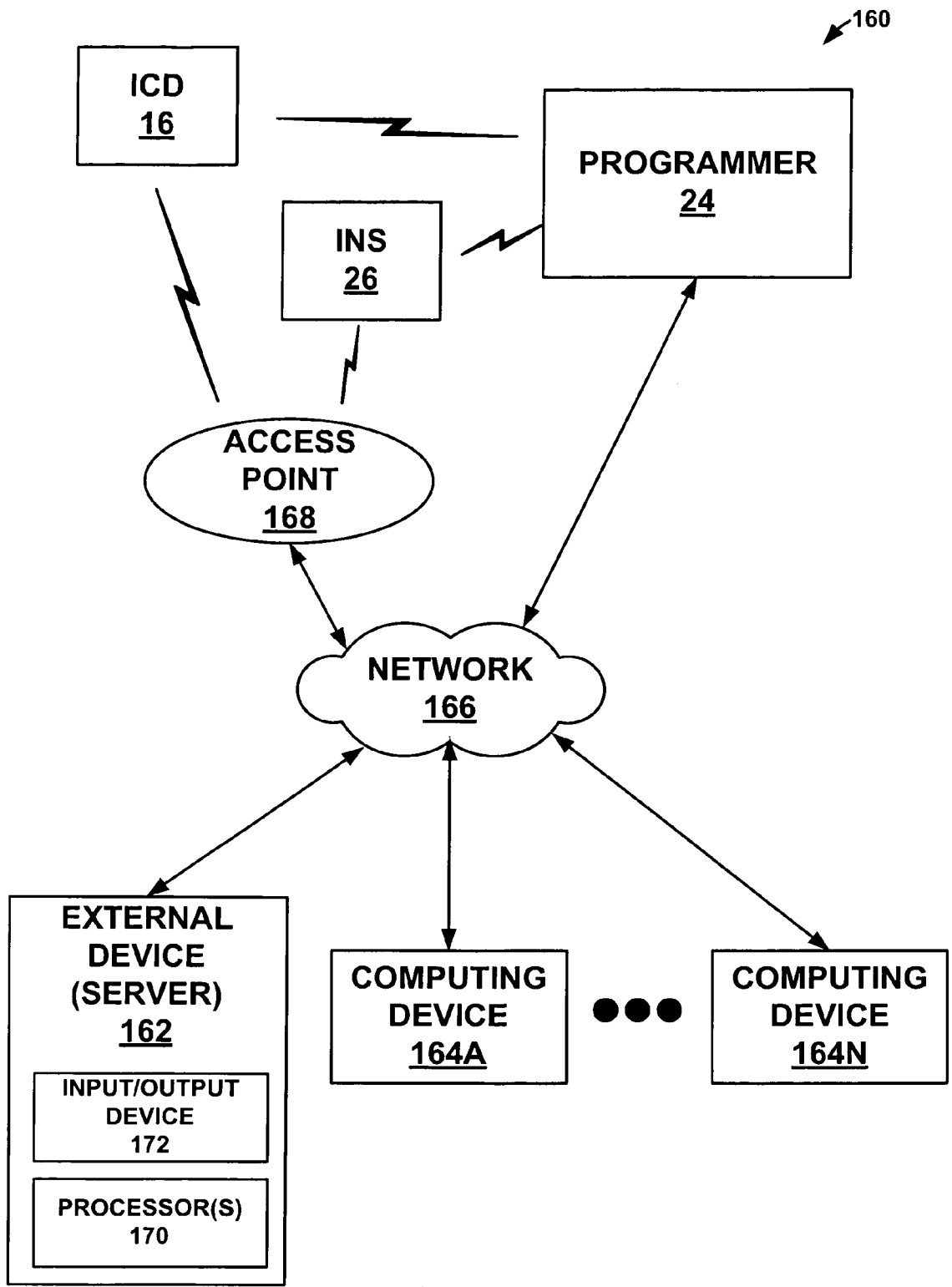
FIG. 13 is a block diagram illustrating an example system that includes an external device, such as a server, and one or more computing devices that are coupled to the INS, ICD, and programmer shown in FIG. 1 via a network.

FIG. 13 is a block diagram illustrating a system 160 that includes an external device 162, such as a server, and one or more computing devices 164A-164N that are coupled to ICD 16, INS 26, and programmer 24 shown in FIG. 1 via a network 166, according to one example. In this example, ICD 16 and INS 26 uses their respective telemetry modules 98 (FIG. 6) and 118 (FIG. 7) to communicate with programmer 24 via a first wireless connection, and to communicate with an access point 168 via a second wireless connection. In the example of FIG. 13, access point 168, programmer 24, external device 162, and computing devices 164A-164N are interconnected, and able to communicate with each other, through network 166.

In some cases, one or more of access point 168, programmer 24, external device 162, and computing devices 164A-164N may be coupled to network 166 through one or more wireless connections. ICD 16, INS 26, programmer 24, external device 162, and computing devices 164A-164N may each comprise one or more processors, such as one or more microprocessors, DSPs, ASICs, FPGAs, programmable logic circuitry, or the like, that may perform various functions and operations, such as those described herein.

Access point 168 may comprise a device that connects to network 166 via any of a variety of connections, such as telephone dial-up, digital subscriber line (DSL), cellular phone network, or cable modem connections. In other examples, access point 168 may be coupled to network 166 through different forms of connections, including wired or wireless connections. In some examples, access point 168 may communicate with programmer 24, ICD 16, and/or INS 26. Access point 168 may be co-located with patient 12 (e.g., within the same room or within the same site as patient 12) or may be remotely located from patient 12. For example, access point 168 may be a home monitor that is located in the patient's home or is portable for carrying with patient 12.

During operation, ICD 16 and/or INS 26 may collect, determine, and store various forms of diagnostic data. For example, as described previously, ICD 16 or INS 26 may collect electrical parameter values indicative of an impedance of the electrical path between ICD 16 and INS 26 and/or a trend (or a rate of change) of the electrical parameter values over time. As previously indicated, the electrical parameter values may include the actual determined impedance or a voltage or current amplitude of a signal sensed by one of the devices 16, 26 based on a signal transmitted by the other device 26, 16. In certain cases, ICD 16 or INS 26 may directly analyze collected diagnostic data and generate any corresponding reports or alerts. In some cases, however, ICD 16 or INS 26 may send the electrical parameter values indicative of impedance, as well as the known characteristics (e.g., voltage and/or current amplitude) of the electrical signal that was transmitted to determined impedance, to programmer 24, access point 168, and/or external device 162, either wirelessly or via access point 168 and network 166, for remote processing and analysis.

For example, ICD 16 may send programmer 24 collected electrical parameter values indicative of transthoracic impedance, which is then analyzed by programmer 24. Programmer 24 may generate reports or alerts after analyzing electrical parameter values and determine whether the values indicate that patient 12 requires medical attention, e.g., based on the electrical parameter values exceeding a threshold value. In some cases, ICD 16, INS 26, and/or programmer 24 may combine all of the diagnostic data into a single displayable transthoracic impedance report, which may be displayed on programmer 24. The transthoracic impedance report may contain information concerning the transthoracic impedance determinations, the time of day at which the determinations were taken, and identify any patterns in the transthoracic impedance determinations. A clinician or other trained professional may review and/or annotate the transthoracic impedance report, and possibly identify any patient conditions (e.g., heart disease).

In another example, ICD 16 or INS 26 may provide external device 162 with collected impedance data via access point 168 and network 166. External device 162 includes one or more processors 170. In some cases, external device 162 may request collected impedance data, and in some cases, ICD 16 or INS 26 may automatically or periodically provide such data to external device 162. Upon receipt of the impedance data via input/output device 172, external device 162 is capable of analyzing the data and generating reports or alerts upon determination that the impedance data indicates a patient condition may exist, a lead-related condition may exist, or that the leads coupled to ICD 16 or INS 26 have moved relative to each other. As previously indicated, in some examples, ICD 16 or INS 26 may generate the alert upon determining that the impedance data indicates a patient condition may exist, that the leads coupled to ICD 16 or INS 26 have moved relative to each other or that a lead-related condition may exist.

In one example, external device 162 may combine the diagnostic data into an impedance report. One or more of computing devices 164A-164N may access the report through network 166 and display the report to users of computing devices 164A-164N. In some cases, external device 162 may automatically send the report via input/output device 172 to one or more of computing devices 164A-164N as an alert, such as an audio or visual alert. In some cases, external device 162 may send the report to another device, such as programmer 24, either automatically or upon request. In some cases, external device 162 may display the report to a user via input/output device 172.

In one example, external device 162 may comprise a secure storage site for diagnostic information that has been collected from ICD 16, INS 26, and/or programmer 24. In this example, network 166 may comprise an Internet network, and trained professionals, such as clinicians, may use computing devices 164A-164N to securely access stored diagnostic data on external device 162. For example, the trained professionals may need to enter usernames and passwords to access the stored information on external device 162. In one example, external device 162 may be a CareLink server provided by Medtronic, Inc., of Minneapolis, Minn.

In each of the systems described above, both ICD 16 and INS 26 include a stimulation generator. In other examples, an electrical parameter value indicative of an impedance of a path between a first IMD and a second IMD may be determined using similar techniques, wherein the second IMD does not include a stimulation generator. Thus, the electrical parameter value indicative of the impedance may be determined by generating an electrical signal between two or more electrodes connected to the first IMD and sensing an electrical signal via the second IMD.

The techniques described in this disclosure, including those attributed to ICD 16, INS 26, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described in this disclosure. These and other examples are within the scope of the following claims.

The invention claimed is:

1. A system comprising:
   a first implantable medical device connected to a first electrode and a second electrode, the first implantable medical device being configured to deliver an electrical signal between the first and second electrodes;
   a second implantable medical device configured to sense the electrical signal; and
   a processor configured to determine an electrical parameter value indicative of an impedance of a path between the first and second implantable medical devices based on the sensed electrical signal, and determine whether a system integrity issue exists based on the electrical parameter value.

2. The system of claim 1, the first implantable medical device being configured to deliver at least one of pacing, cardioversion or defibrillation therapy to a heart of a patient and the second implantable medical device being configured to deliver electrical stimulation to a tissue site within the patient.

3. The system of claim 2, wherein the tissue site comprises at least one of a nonmyocardial tissue site or a nonvascular cardiac tissue site.

4. The system of claim 1, the first implantable medical device being configured to deliver electrical stimulation to a tissue site within a patient and the second implantable medical device being configured to deliver at least one of pacing, cardioversion or defibrillation therapy to a heart of the patient.

5. The system of claim 1, wherein the processor is configured to determine whether a system integrity issue exists by at least determining whether electrodes connected to the first implantable medical device have moved relative to electrodes connected to the second implantable medical device based on the electrical parameter value.

6. The system of claim 1, wherein the system integrity issue comprises a lead-related condition.

7. The system of claim 6, wherein the lead-related condition comprises at least one of a fractured conductor of a lead or a change in the electrical insulation separating one or more conductors within the lead.

8. The system of claim 1, wherein the processor is configured to determine whether the electrical parameter value is within a predetermined range of values, determine that the system integrity issue exists if the electrical parameter value is not within the predetermined range of values, and generate an indication if the electrical parameter value is not within the predetermined range of values.

9. The system of claim 8, wherein the processor is configured to generate the indication via at least one of the implantable medical device or an external device.

10. The system of claim 8, further comprising:
a memory that stores a plurality of ranges of values and associated patient activity levels or posture levels; and
a sensor configured to generate a sensor signal indicative of patient activity level or posture, wherein the processor is configured to determine the patient activity level or posture based on the sensor signal and select the predetermined range of values from the memory based on the determined patient activity level or posture.

11. The system of claim 1, wherein the processor is configured to determine a rate of change of the electrical parameter value over time and generates an indication if the rate of change exceeds a threshold value.

12. The system of claim 1, wherein the impedance comprises a transthoracic impedance of a patient in which the first and second implantable medical devices are implanted.

13. The system of claim 1, wherein the electrical signal comprises a signal characteristic that is less than a tissue activation threshold of a patient in which the first and second implantable medical devices are implanted.

14. The system of claim 1, wherein the first medical device comprises the processor.

15. The system of claim 1, wherein the second medical device comprises the processor.

16. The system of claim 1, further comprising a medical device programmer comprising the processor.

17. The system of claim 1, wherein the processor is configured to control at least one of the first or second implantable medical devices to deliver therapy to a patient based on the electrical parameter value.

18. The system of claim 1, wherein the processor is configured to modify a therapy parameter of at least one of the first or second implantable medical devices based on the electrical parameter value.

19. The system of claim 1, wherein the processor is configured to store at least one of the electrical parameter value or a trend in the electrical parameter value over time in a memory.

20. The system of claim 1, wherein the processor is configured to determine a trend in the electrical parameter value over time.

21. The system of claim 20, wherein the processor is configured to transmit data indicative of the trend in the electrical parameter value over time to a user.

22. The system of claim 1, wherein the electrical signal comprises a first electrical signal and the electrical parameter value comprises a first electrical parameter value, and wherein the first implantable medical device is connected to a third electrode and a fourth electrode, the first implantable medical device being configured to deliver a second electrical signal between the third electrode and the fourth electrode and the second implantable medical device being configured to sense the second electrical signal, wherein the processor is configured to determine a second electrical parameter value based on the second electrical signal and determine whether the system integrity issue exists based on the first and second electrical parameter values.

23. The system of claim 22, wherein the processor is configured to determine whether the system integrity issue exists based on a ratio of the first and second electrical parameter values.

24. The system of claim 1, wherein the processor is configured to generate a system integrity indication in response to determining the system integrity issue exists based on the electrical parameter value.

25. A system comprising:
means for delivering an electrical signal between a first electrode and a second electrode of a first implantable medical device;
means for sensing the electrical signal at a second implantable medical device; and
means for determining an electrical parameter value of a path between the first and second implantable medical devices based on the sensed electrical signal; and
means for determining whether a system integrity issue exists based on the electrical parameter value.

26. The system of claim 25, wherein the means for determining whether a system integrity issue exists based on the electrical parameter value determines whether the system integrity issue exists by at least determining whether the first implantable medical device and the second implantable medical device have moved relative to each other, or whether electrodes connected to the first and second implantable medical devices have moved relative to each other based on the electrical parameter value.

27. The system of claim 25, wherein the system integrity issue comprises a lead-related condition.

28. A method comprising:
delivering an electrical signal between a first electrode and a second electrode connected to a first implantable medical device;
sensing the electrical signal with a second implantable medical device; and
determining an electrical parameter value indicative of an impedance of a path between the first and second implantable medical devices based on the sensed electrical signal.

29. The method of claim 28, the first implantable medical device being configured to deliver at least one of pacing, cardioversion or defibrillation therapy to a heart of a patient and the second implantable medical device being configured to deliver electrical stimulation to a tissue site within the patient.

30. The method of claim 29, wherein the tissue site comprises at least one of a nonmyocardial tissue site or a nonvascular cardiac tissue site.

31. The method of claim 28, the first implantable medical device being configured to deliver electrical stimulation to a tissue site within a patient and the second implantable medical device being configured to deliver at least one of pacing, cardioversion or defibrillation therapy to a heart of the patient.

32. The method of claim 28, further comprising determining whether electrodes connected to the first implantable medical device have moved relative to electrodes connected to the second implantable medical device based on the electrical parameter value.

33. The method of claim 32, wherein determining whether electrodes connected to the first implantable medical device have moved relative to electrodes connected to the second implantable medical device comprises comparing the electrical parameter value to a threshold value.

34. The method of claim 28, further comprising determining a presence of a lead-related condition based on the electrical parameter value.

35. The method of claim 28, further comprising determining whether the electrical parameter value is within a predetermined range of values, and generating an indication if the electrical parameter value is not within the predetermined range of values.

36. The method of claim 35, further comprising:
determining a patient posture or a patient activity level; and
selecting the predetermined range of values based on the patient posture or a patient activity level.

37. The method of claim 28, further comprising determining a rate of change of the electrical parameter value over time and generating an indication if the rate of change exceeds a threshold value.

38. The method of claim 28, wherein the impedance comprises the impedance of an electrical path between at least one of the first electrode or the second electrode connected to the first implantable medical device and a third and a fourth electrode connected to the second implantable medical device.

39. The method of claim 28, wherein the electrical signal comprises a signal characteristic less than a tissue activation threshold of a patient in which the first and second implantable medical devices are implanted.

40. The method of claim 28, further comprising controlling at least one of the first or second implantable medical devices to deliver therapy to a patient based on the electrical parameter value indicative of the impedance of the path between the first and second implantable medical devices.

41. The method of claim 28, further comprising modifying therapy delivery by the first or second medical devices based on the electrical parameter value.

42. The method of claim 41, wherein modifying therapy delivery by the first or second medical devices based on the electrical parameter value comprises suspending therapy delivery by the first or second medical devices based on the electrical parameter value.

43. The method of claim 28, further comprising generating an indication to a user based on the electrical parameter value.

44. The method of claim 28, wherein the electrical signal comprises a first electrical signal and the electrical parameter value comprises a first electrical parameter value, and wherein the first and second electrodes define a first electrode combination, the method further comprising:
delivering a second electrical signal between electrodes of a second electrode combination connected to the first implantable medical device, wherein the second electrode combination comprises at least one different electrode than the first electrode combination;
sensing the second electrical signal with the second implantable medical device;
determining a second electrical parameter value indicative of the impedance of the path between the first and second implantable medical devices based on the sensed second electrical signal; and
detecting movement of the first and second implantable medical devices relative to each other or movement of leads connected to the first and second implantable medical devices relative to each other based on the first and second electrical parameter values.

45. The method of claim 28, wherein the electrical signal comprises a first electrical signal and the electrical parameter value comprises a first electrical parameter value, and wherein sensing the first electrical signal with the second implantable medical device comprises sensing the first electrical signal via a first electrode combination including electrodes connected to the second implantable medical device, the method further comprising:
delivering a second electrical signal between the first and second electrodes connected to the first implantable medical device;
sensing the second electrical signal with a second electrode combination including electrodes connected to the second implantable medical device, wherein the second electrode combination comprises at least one different electrode than the first electrode combination;
determining a second electrical parameter value indicative of the impedance of the path between the first and second implantable medical devices based on the sensed second electrical signal; and
detecting movement of the first and second implantable medical devices relative to each other or movement of leads connected to the first and second implantable medical devices relative to each other based on the first and second electrical parameter values.

46. The method of claim 28, further comprising determining a trend in the electrical parameter value over time and transmitting data indicative of the trend in the electrical parameter value over time to a user.

* * * * *